United States Patent [19]

Bowman

[11] 4,059,982
[45] Nov. 29, 1977

[54] APPARATUS FOR THE MEASUREMENT OF THERMAL PROPERTIES OF BIOMATERIALS

[75] Inventor: Harry Frederick Bowman, Needham, Mass.

[73] Assignee: Massachusetts Institute of Technology, Cambridge, Mass.

[21] Appl. No.: 608,954

[22] Filed: Aug. 29, 1975

[51] Int. Cl.² ................... G01F 1/68; G01N 25/18
[52] U.S. Cl. ............................... 73/15 A; 73/204
[58] Field of Search .............. 73/15 R, 15 A, 27 R, 73/190, 204

[56] References Cited

U.S. PATENT DOCUMENTS

| | | | |
|---|---|---|---|
| 1,691,600 | 11/1928 | Brush, Jr. | 73/204 |
| 2,728,337 | 12/1955 | Guillemin, Jr. | 73/27 |
| 2,892,347 | 6/1959 | Laprand | 73/204 |
| 3,138,025 | 6/1964 | Figerson | 73/204 |
| 3,595,079 | 7/1971 | Grahn | 73/204 |
| 3,803,913 | 4/1974 | Tracer | 73/204 |
| 3,821,643 | 7/1974 | Derry et al. | 73/15 |

OTHER PUBLICATIONS

Parr, "A Hot Wire Anemometer for Low Wind Speeds" in Journal of Sci. Inst. vol. 24, 12/47, pp. 317-319.

Lumley, "The Const. Temperature Hot-Thermistor Anemometer" in Symposium on Measurement in Unsteady Flow, 5/62, pp. 75-82.

*Primary Examiner*—Herbert Goldstein
*Attorney, Agent, or Firm*—Arthur A. Smith, Jr.; Martin M. Santa; Robert F. O'Connell

[57] ABSTRACT

Appropriate heating and temperature sensing means are immersed in a medium the thermal conductivity, $k$, and thermal diffusivity, $\alpha$, of which are to be determined both in the presence of and in the absence of a flow of fluid therethrough. The method and system used for making such measurements operate in accordance with a thermal model of the heating means and the medium wherein the heating means is treated as a distributed thermal mass and wherein heat conduction occurs in a coupled thermal system which comprises both the heating means and the adjacent region of the medium which surrounds such heating means. The thermal conductivity of the medium is determined as a function of the temperature difference between the temperature of the unheated medium and the temperature of the heated medium, of the resistance of the heating means, of the power applied to the heating means, of the thermal conductivity of the heating means and of the radius of a spherical heating means having a volume equivalent to that of the actual heating means. In accordance with various embodiments of the invention the temperature difference and heating means resistance are maintained constant or are permitted to vary with time over the time period of measurement. Measurements of the thermal conductivity in the presence and in the absence of fluid flow permit a further measurement to be made of the rate of flow, $\dot{\omega}$, of a fluid which is flowing through the medium.

32 Claims, 18 Drawing Figures

$$T = \sum_n C_n R^n$$

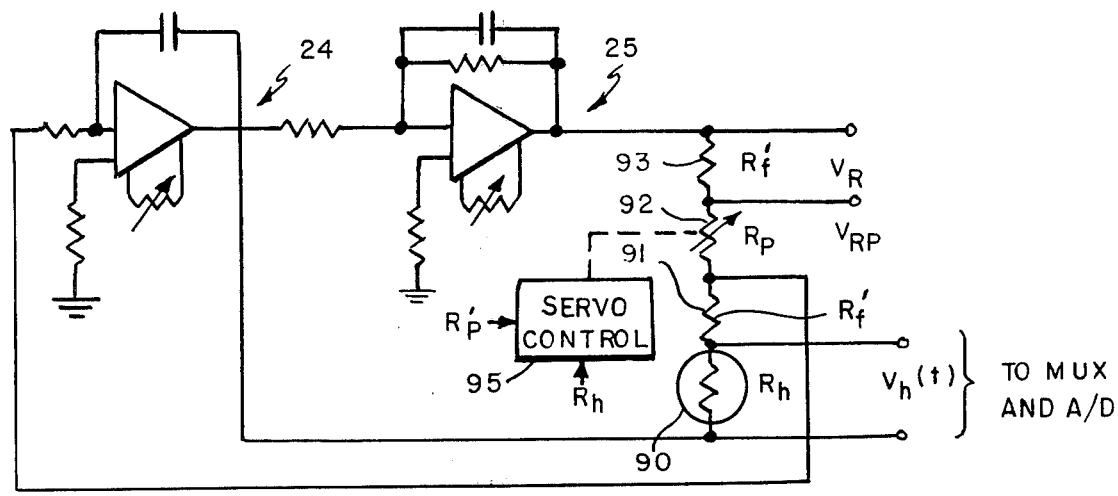
FIG. 10A
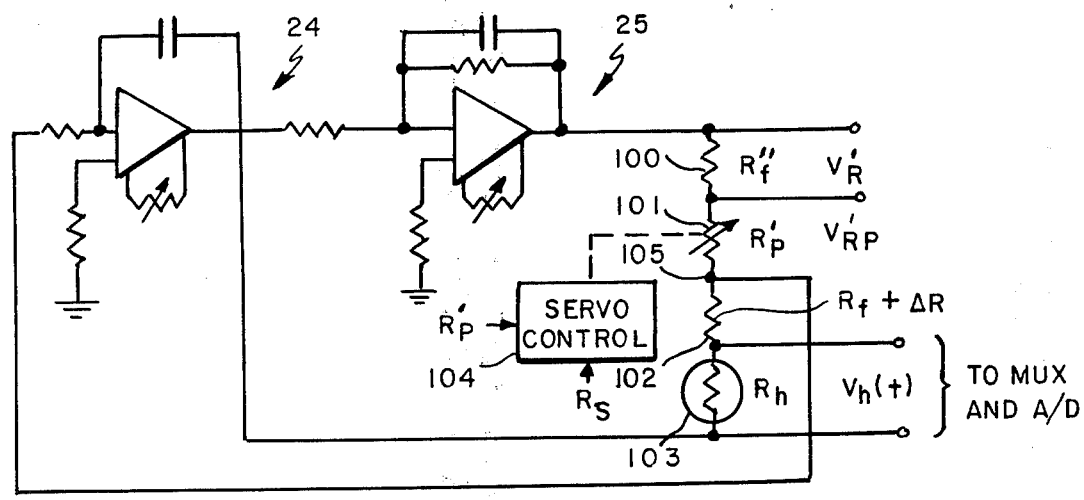
FIG. 15
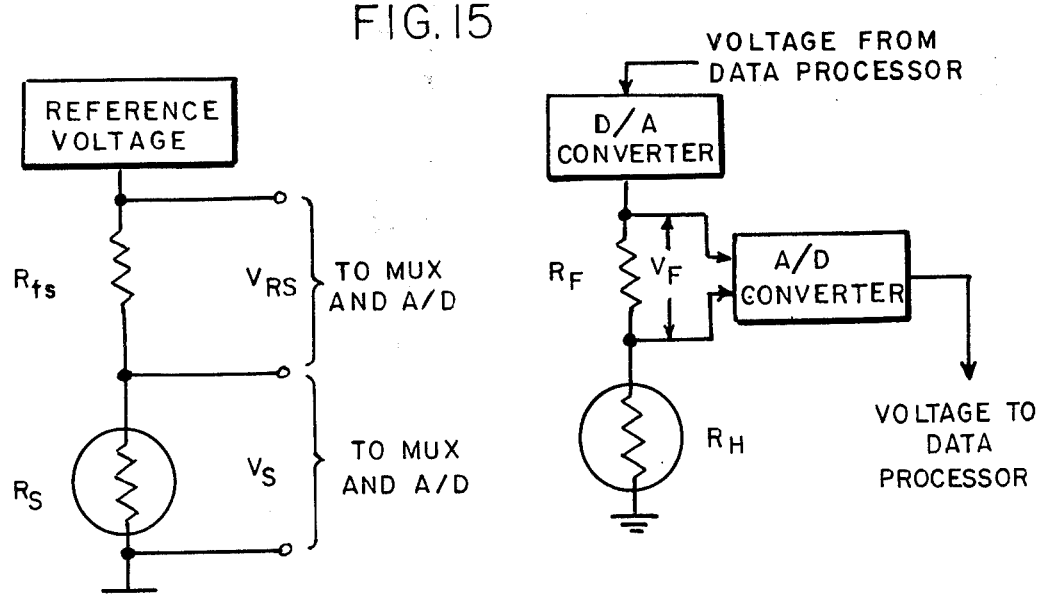
FIG. 10B
FIG. 12

APPARATUS FOR THE MEASUREMENT OF THERMAL PROPERTIES OF BIOMATERIALS

The invention herein described was made in the course of work performed under a grant from the National Institute of Health.

INTRODUCTION

This invention relates generally to techniques for determining the thermal properties of materials, as well as other properties related to or derived from such thermal properties and, more particularly, methods and apparatus for determing primarily the thermal conductivity and thermal diffusivity of materials, in the presence or in the absence of fluid flow therein, and the flow rate of fluids flowing therein.

BACKGROUND OF THE INVENTION

A knowledge of the thermal properties of biomaterials has long been considered important to researchers and others interested in increasing man's understanding of the nature of materials and their thermal interactions, as well as to designers of equipment and systems in which the thermal characteristics of the materials used therein or operated thereon are of significance. For example, important information concerning biological materials, such as human and animal tissues, can be obtained from knowledge of the thermal properties thereof.

Thus, it is known that biomaterials are capable of heat transfers by virtue of a temperature gradient, such heat transfer capability being especially important in living biomaterials because the state of life thereof, for example, may depend on the maintenance of a specific temperature level. Heat transfer by conduction is usually most important in determining the heat transfer within the biological medium and such heat transfer is best characterized in the steady-state by the thermal conductivity, $k$, of the medium and in the non-steady state of its thermal diffusivity, $\alpha$. Since there is no presently known method of determining $k$ and $\alpha$ of a biomaterial from a knowledge of some other fundamental property or properties thereof, it is necessary to devise appropriate processes and apparatus to measure $k$ and $\alpha$ in some appropriate manner. Accordingly, there has been an increasing utilization, particularly in medical research and clinical laboratories, of processes which require heat transfer through biological materials, such as in cryobiology (e.g., cryosurgery), in tissue and organ preservation, and in frostbite studies, for example. Other procedures which are heat transfer dependent and, thus, require a knowledge of thermal properties include clinical applications of ultrasonic wave energy, microwave energy and laser beam energy in both diagnostic and therapeutic operating modes.

Such processes require more extensive and more reliable information concerning the thermophysical properties of such materials and, in particular, information concerning the thermal conductivities and thermal diffusivities thereof which permit the determination of temperature distributions, heat transfer rates and, in turn, the flow rates of fluids through the biological medium. It is particularly important, for example, to monitor the flow rate of blood through tissue so that flow disturbances can be monitored and corrective action taken in cases where maldistribution of blood flow in a patient would have unfavorable and possibly fatal consequences.

Techniques which have been applied to the measurement of properties of biological materials have included both invasive and non-invasive techniques. A general summary of such techniques and the limitations thereof is presented in the text, *Annual Review of Biophysics and Bioengineering*, "Theory, Measurement and Application of Thermal Properties of Biomaterials," H. Frederik Bowman et al., pp. 43–80, Vol. 4, 1975. While non-invasive techniques can provide information on thermal properties, they are necessarily limited to regions near the surface of the materials and, in order to obtain reliable information on thermal properties below the surface, invasive techniques are required. Such invasive techniques involve the implantation within the specimen material of heat sources (or sinks) which may also serve as temperature sensors. Probes which have been utilized for this purpose include the thermal comparator, the heated thermocouple and the heated thermistor. Up to now, however, no successful thermistor probe method and apparatus have become available which can provide realistic measurements of such thermophysical properties because of the limitations inherent in the thermal models which have heretofore been used in the analysis of the structure and operation of the probes and the media into which they are inserted.

For example, in the article "A Method for the Measurement of Thermal Properties of Biological Materials" by J.C. Chato, ASME Symposium on Thermal Problems in Biotechnology, LC No. 68-58741, 1968, Chato discusses the use of a thermistor probe, particularly in studying the thermal properties of biomaterials, and suggests that the probe technique has potential for measuring not only the thermal conductivity ($k$) thereof but also the thermal inertia (i.e., $\sqrt{k\rho c}$) and the flow rate ($\omega$) of blood as well. In utilizing the functional relationship between input power and probe temperature used in such technique, Chato assumed the thermistor bead to be a lumped thermal mass and using such assumption solved the heat conduction equation for the surrounding medium only. The Chato approach assumed a constant bead surface temperature at all times greater than zero and equal to a spatially uniform temperature rise in the bead.

While in principle the application of the solution of the heat conduction equation to the experimental data was expected by Chato to yield thermal conductivity and thermal inertia values, the assumption of a thermal model in which the thermistor bead was treated as a lumped thermal mass and the solving of the heat conduction equation solely for the surrounding medium was found by Bowman to be inadequate. Because of the inherent limitations in the thermal model, no meaningful measurements were able to be made of the desired thermal properties using the Chato techniques and, accordingly, the technique proved unsuccessful.

BRIEF DESCRIPTION OF THE INVENTION

In accordance with this invention a different thermal model is developed and a different implementation of the solution of the heat conduction equations utilizing a thermistor probe is designed to provide a more realistic representation of the thermal properties of the thermistor bead and the surrounding medium so as to produce a more accurate measurement of such properties as thermal conductivity and thermal diffusivity form which other thermal properties and states of flow can be derived. In accordance with the invention a thermal model is devised which treats the thermistor bead of the probe as a distributed thermal mass and the heat conduction equation is solved for both the interior of the bead as well as the region of the medium surrounding it.

If a thermistor bead is placed in a medium and the bead and the region of the medium surrounding it assume an initial equilibrium, or reference, temperature, the temperature of the bead and medium can be raised to a predetermined level above the equilibrium temperature by applying electrical energy to the bead which thereupon thermally dissipates in the bead and its surrounding medium. If the temperature rise is to be maintained at the desired level, the electrical energy must be dissipated at a rate which is sufficient to maintain the temperature at the desired level and the electrical power required for such purpose depends on the heat transfer characteristics of the surrounding medium. Thus, if the characteristics of the medium are such as to enhance the heat transfer, a greater amount of electrical power will be needed to maintain the desired temperature increment between the reference temperature and the temperature at the desired perdetermined level, while, if the characteristics thereof are such as to impede heat transfer, less electrical power will be needed to maintain the temperature increment.

In a biological medium such as human or animal tissue, for example, the heat transfer capability of the medium depends upon the intrinsic thermal conductivity of the medium, the local blood flow rate in the medium and the specific heat of the blood therein, such characteristics contributing to a property which, for convenience, can be referred to as the "effective thermal conductivity" of the medium. Such term can be defined as a measure of the rate at which heat is being removed from the bead by (or transported through) a medium in the presence of fluid flow in the medium. Such property can be contrasted with the "intrinsic thermal conductivity" therefore which can be defined as a measure of the rate at which heat can be removed from the bead by (or transported through) a medium in the absence of any fluid flow therein (e.g., a biologic medium in which no blood flow is present).

In accordance with the invention the effective thermal conductivity and the effective thermal diffusivity of a medium can be obtained, as well as the flow rate of a fluid flowing in the medium by the use of unique processes and apparatus for implementing such processes which are described and in more detail below. The determination of thermal conductivity and thermal diffusivity, for example, can be made by using a single thermistor bead which acts both as a temperature sensor element and as a heating element for raising the temperature of the bead which is immersed in a medium to the desired mean temperature above an initial reference medium temperature. Since the reference temperature will not vary to any substantial extent over a relatively short time period (e.g., less than one minute or so), such determination can be made using relatively short time measurements and calculations with the use of only a single bead operating both as a temperature sensor and as a heater element.

In accordance therewith the initial reference temperature of the bead and medium is determined and power is applied thereto to raise the mean temperature of the bead to a fixed predetermined level. The power input to the bead is regulated by an electronic control circuit so that the predetermined mean temperature thereof is reached rapidly and is maintained at the desired, constant level above the reference temperture. Any variations in the desired temperature level are appropriately sensed so that the controller can then increase or reduce the input power to the thermistor bead thereby driving the thermistor resistance to a value which maintains the temperature thereof at the desired level.

The variable voltage which is supplied to the thermistor probe is appropriately converted to digital form and is used as digital input information to a data processor which is arranged to calculate both the thermal conductivity and the thermal diffusivity in accordance with expressions derived from solutions to the heat conduction equations arrived at by using a thermal model which takes into account the distributed thermal mass of the thermistor bead and the solutions of the equations both for the interior of the bead and for the surrounding region of the medium. Such equations and the solutions thereof are described in the article "Temperature Field Due to a Time Dependent Heat Source of Spherical Geometry in an Infinite Medium" by T.A. Balasubramaniam and H.F. Bowman, *Journal of Heat Transfer*, Transactions of the ASME, Paper No. 74-HT-CC. The caculations required by the data processing system are uniquely determined by such a thermal model representation and the system thereupon provides outputs which represent the thermal conductivity and thermal diffusivity of the medium being examined.

The invention can also provide other important thermal and non-thermal properties thereof which can be derived from a determination of thermal conductivity. Thus, the flow rate of a fluid which moves through the medium (e.g., the flow rate of blood through a biologic medium) can be calculated in accordance with an expression also derived from solutions to the heat conduction equations which specifically include blood flow as a variable in such a thermal model representation. Information concerning such flow rates is optimally required on a substantially continuous basis over a relatively long time period, much longer than the time periods required to determine the thermal conductivity and thermal diffusivity, per se, of the medium. Because the reference temperature of the medium tends to vary over such longer time periods, the temperature difference between the desired heated mean temperature level and the reference temperature will also vary. Since the determination of the thermal conductivity and, hence, the determination of the flow rate depends on a determination of such temperature difference, the process of determining flow rate requires either that the reference temperature be continuously measured while the heated mean temperature of the thermistor bead is maintained constant and the temperature difference appropriately calculated or that such temperature difference itself be maintained substantially constant over the time period during which flow rate information is obtained.

In either case, two elements (generally thermistor beads) are required, one for sensing the reference temperatures of the medium and the other to serve as a heat source which will be heated to the desired mean temperature level. As discussed in more detail below, while the continuous calculation of a time varying temperature difference can be achieved, a significant variation in the temperature difference itself can impose an influence on the flow rate which is being determined and thereby affects the accuracy of the determination which is being made. Accordingly, it is preferable to maintain the temperature difference substantially constant by using an appropriate control circuit therefor, as described below, or, alternatively, to maintain the difference between the resistances of the heater thermistor bead and the sensor thermistor bead substantially constant which process, in effect, maintains a substantially constant temperature difference therebetween.

The values of thermal conductivity, thermal diffusivity and flow rate can be appropriately displayed, as desired, and the overall logic circuitry for the data processing system which implements the required calculations in accordance with the thermal model can be appropriately packaged together with the thermistor probe unit and control circuitry to provide a suitably small and portable apparatus for use in a laboratory, hospital, emergency station, industry or other facility at a reasonable cost. Such values can be displayed either intermittently or continuously. The probe design and the small size makes the use thereof relatively non-traumatic in living tissue.

While the particular embodiments of the invention are, for convenience, described herein with reference to the determination of thermal and non-thermal properties of biological materials, it is understood that the techniques so disclosed are not limited to use only with such materials but are also applicable to other media and fluids fowing therein as well.

The invention can be described in more detail with the help of the drawings wherein:

FIG. 10A shows a partial schematic and partial block diagram of a control circuit which can be used in another embodiment of the invention;

FIG. 10B shows a schematic of a portion of the embodiment of FIG. 11;

FIG. 12 shows a schematic diagram of another embodiment of a control circuit which is an alternative to that shown in FIG. 10A;

FIG. 15 shows a partial schematic and partial block diagram of a control circuit which can be used in implementing the method of the flow chart of FIG. 14.

Figure 1:
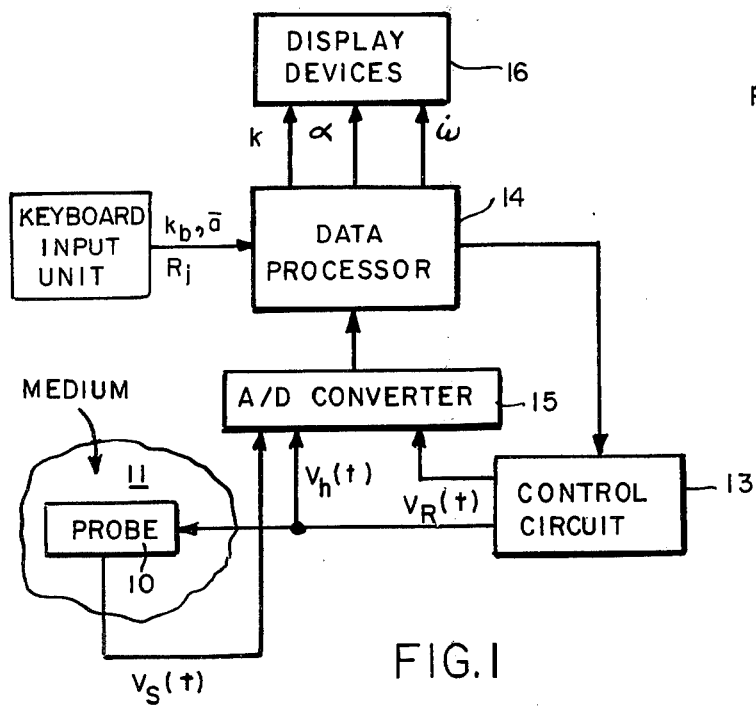
FIG. 1 shows a broad block diagram of one particular embodiment of the invention.

In accordance with the invention, as broadly shown in FIG. 1, a thermistor probe 10, utilizing one or more thermistor beads, is immersed in a medium 11, such as a biological medium, so as to form a coupled system consisting of the thermistor bead or beads and the surrounding region or regions of the medium corresponding thereto. The thermistor probe may utilize, for example, a single bead which operates as both a temperature sensor and a heater element. Alternatively, the probe may utilize a first sensor bead which operates as a reference temperature sensor and a second heater bead which operates as a heat source. When the probe is immersed in the medium, a time dependent voltage $V_h(t)$ is supplied by a control circuit 13 to the appropriate heater bead to rapidly raise the mean temperature thereof to a desired level above the initial equilibrium level. The power that must be dissipated in the electrically resistive element making up such bead in order to maintain the elevated temperature of the bead at such level depends upon the effective thermal conductivity of the surrounding medium.

In accordance with the thermal model of the invention, the thermistor heater bead is treated as a distributed thermal mass and the heat conduction equations are solved for the overall coupled thermal system, i.e., the thermal system which includes both the interior of the heater bead and the region of medium surrounding it. The measured electrical resistance of the heater bead of the thermistor probe and, hence, the corresponding temperature of the bead, is in reality a volume mean value.

Figure 2A:
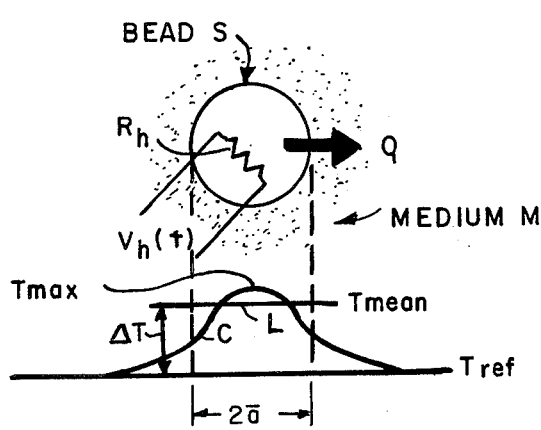
FIGS. 2A and 2B show diagrammatic representations of the characteristics of the thermal model in accordance with the invention.
Figure 2B:
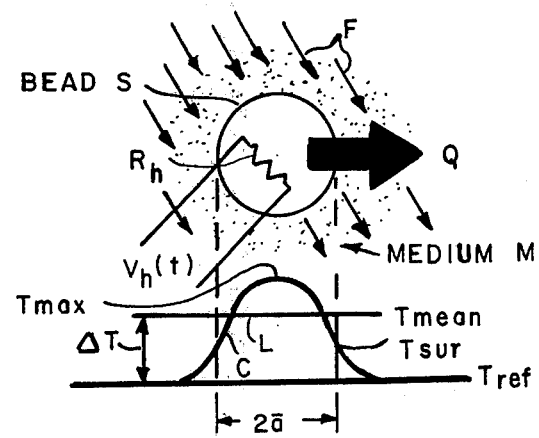

In order to understand the characteristics of such thermal model it is helpful to consider the representation of the probe and medium shown in FIGS. 2A and 2B. As can be seen in FIG. 2A, if a thermistor heater bead, schematically and ideally represented by a sphere S having a resistance $R_h$, is immersed in a biological medium M, for example, having an equilibrium, or reference, temperature $T_{ref}$ in the absence of any fluid flow therein, there is a voltage $V_h(t)$ which, when applied thereto, will raise the temperature of the bead to a value above the reference level. Heat is thereupon transferred from the bead to the medium, as shown by the arrow Q. In accordance with the thermal model the bead is considered as a distributed thermal mass rather than as a lumped thermal mass, as assumed by Chato, and the temperature distribution can be generally represented by a curve C as shown in FIG. 2A, wherein $T_{max}$ occurs at the center of the spherical bead S and wherein the temperature decreases in all directions therefrom to the reference temperature $T_{ref}$ in the region of the surrounding medium which is removed from the center of the bead. The mean temperature $T_{mean}$ of the bead is shown by line L which is at a level $\Delta T$ above the reference temperature.

As shown in FIG. 2B, in the presence of fluid flow F in the medium, heat is transferred more rapidly from the bead to the medium (i.e., Q is greater) and a greater voltage $V_h(t)$ is required to maintain the same mean temperature at the bead (shown by line L) at a level $\Delta T$ above the reference temperature. The shape of the temperature distribution curve C in the bead and the immediately surrounding region of medium is different in the presence of fluid flow. As seen in FIG. 2B, under such conditions, a higher $T_{max}$ occurs at the center of the bead and the temperature $T_{sur}$ at the surface of the bead drops to a lower level than that at the bead surface in an equivalent medium in the absence of fluid flow.

The temperature distribution curve of such a thermal model can be contrasted with that assumed by Chato wherein a single heat conduction equation is solved for the medium only and the temperature distribution is represented as being constant throughout the bead with no thermal gradient assumed to exist in the bead itself, and the bead-medium interface temperature is assumed to be independent of the thermal properties of the medium.

In accordance with such thermal model one embodiment of the invention can be described for determining the thermal conductivity of the medium in the presence of fluid flow in the medium (i.e., the "effective" thermal conductivity) and in the absence of fluid flow (i.e., the "intrinsic" thermal conductivity). In accordance therewith and using a single thermistor bead, the temperature of the bead is raised from an initial reference value to a predetermined constant value above the initial reference value, by the application of an appropriate current which drives the bead to a predetermined resistance and therefore temperature and is maintained thereat by a control circuit which either increases or decreases the current supplied thereto to continuously control the bead resistance value and to change such value so that a predetermined desired mean temperature level is maintained in the bead.

The voltage across the bead which is required provides a parameter from which a determination of the effective thermal conductivity then can be made. By appropriate processing thereof, for example, by a digital data processor 14 (see FIG. 1) which may be in the form of a generalized central computation facility, a mini computer, or a self contained microprocessor to which the voltage $V_h(t)$ is supplied in digital form via a suitable analog-to-digital converter 15, the desired quantities representing the effective or intrinsic thermal conductivity can be determined and displayed by one or more appropriate display devices 16.

Before describing the structure and operation of a specific controller and data processing system which can be used in an embodiment of the invention for providing such determination, it is helpful to describe the steps which are performed for such purpose.

Figure 3:
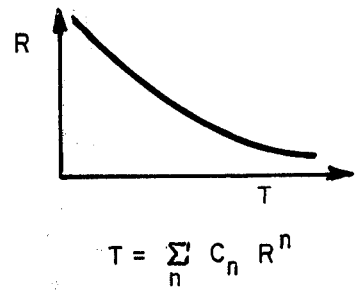
FIG. 3 shows an exemplary and qualitative representative curve of resistance versus temperature of a thermistor element useful in the invention.

First of all, a suitable thermistor probe having a single bead used as both a heater element and a sensor element can be selected, fabricated and calibrated so that the resistance R versus temperature T characteristics of such bead can be obtained in accordance with an exemplary curve, such as depicted qualitatively in FIG. 3, the curve of which follows the general form $$T = \sum_n C_n R^n,$$

or alternatively expressed as $$R = \sum_n C_n' T^n$$

where $C_n$ and $C_n'$ are the constant coefficients of the polynomial expansions represented thereby, the values of which coefficients can be suitably stored in the data processor 14 for the particular thermistor bead which is used.

The thermistor bead is then immersed in the medium of interest and used to obtain the initial reference temperature $T_i$ of the region of immersion.

Figure 4:
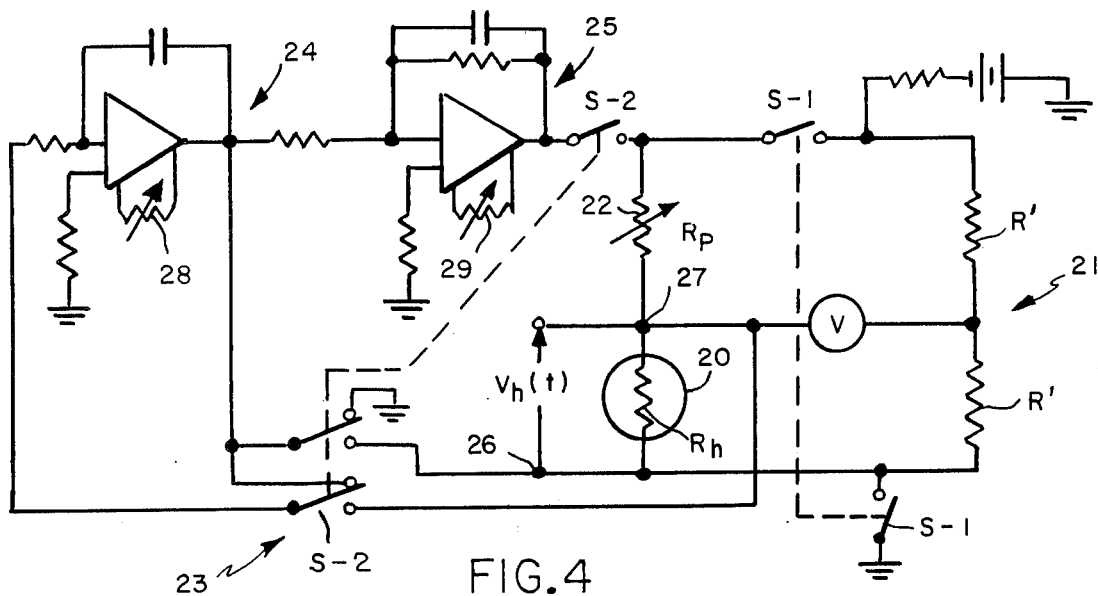
FIG. 4 shows a partial schematic and partial block diagram of a control circuit which can be used in one embodiment of the invention.

As seen in the circuitry of FIG. 4, in determining the initial reference temperature $T_i$, with a nonheating current applied to the bead 20, the bead having an initial reference resistance $R_i$ is used as part of a bridge cirucit 21 in series with a potentiometer 22 having a variable resistance $R_p$. Fixed resistors R' having equal resistances are used in the remaining branches of the bridge circuit. With ganged switches S-1 closed and ganged switches S-2 open, the resistance $R_p$ is varied until a bridge balance is obtained. When balanced, the resistance $R_p$ is suitably measured, for example, by an accurate high impedance resistance measuring device, the value thereof thereby representing the value of $R_1$. The reference temperature $T_i$ of the bead can then be calculated from its temperature v. resistance curve. A predetermined desired temperature difference $\Delta T$ between the temperature of the bead after heating and the initial temperature can be selected and the required final temperature $T_h$ can be calculated as:

$$T_h = T_i + \Delta T$$

The required resistance $R_h$ of the thermistor bead at the calculated temperature $T_h$ can be determined from the resistance versus temperature curve.

The initial steps in measuring the parameters that are used to determine thermal conductivity consist of
1. zero adjusting the offset potentiometes 28 and 29 in the operational amplifier circuits;
2. setting the resistance of the variable potentiometer $R_p$ equal to the required resistance $R_h$; and
3. removing the variable potentiometer 22 and the bead 20 from the bridge circuit by the opening of ganged switches S-1.

The measurement cycle is started by closing ganged switches S-2 and the control circuit thereupon operates to apply the voltage $V_h(t)$ across the bead so as to bring the temperature of the bead rapidly to the correct level in accordance with the required resistance $R_h$. The feedback control circuit 23 of FIG. 4 is arranged to maintain the resistance of the bead 20 at a value equal to that at which the variable potentiometer has been set, i.e., at the desired value of $R_h$. The above adjustments and switch closings can be accomplished either manually or automatically.

The thermal conductivity $k_b$ of the bead itself at the heated temperature $T_h$ can be predetermined in accordance with techniques known to those in the art. A quantity $\bar{a}$ which is the radius of a spherical bead which has a volume equivalent to the volume of the bead which is actually used can also be precalculated. Thermistor beads as generally available at present are of a substantially prolate spheriod shape and, in accordance with the thermal model used, a volume-equivalent spherical-shaped bead is used in solving the heat conduction equations for the coupled thermal system comprising both the bead and the medium. Alternatively, both $k_b$ and $\bar{a}$ can be calculated using two or more media of known thermal properties in a standard calibration procedure.

The control circuitry of FIG. 4 includes a first operational amplifier circuit 24 the output of which is supplied to a second operational amplifier circuit 25, the output of which is fed to the series combination of variable potentiometer 22 and bead 20 via one of ganged switches S-2 when the switches are in their closed positions.

The currents from the potentiometer 22 and the bead 20 appear at the common junction point 27. Their algebraic sum is fed back to the input of operational amplifier 24 as an error signal. When switches S-2 are first closed and switches S-1 are open, an error signal exists at such point (i.e., the resistance of the bead 20 differs from the resistance of potentiometer 22), which results in a voltage supplied to the series combination of potentiometer 22 and thermistor bead 20 at the output of operational amplifier 25 that increases or decreases, depending upon the sign of the summation, or current error signal, until the resistance of the thermistor bead 20 reaches a value equal to that of the potentiometer 22. The voltage $V_h(t)$ across the bead which is required to maintain such error signal substantially at zero is available between the terminals 26 and 27.

A typical appropriate thermistor bead may comprise a glass coated thermistor bead of about 750 ohms nominal resistance, a typically useful type of bead being that made by Fenwal Company, Waltham, Massachusetts, under the designation of Model No. GD31SM2. Such a thermistor bead has the shape of a prolate spheroid having a volume equivalent to the volume of a sphere having a radius $\bar{a}$ of 0.053 cm. The circuitry of FIG. 4 achieves substantially a constant bead resistance $R_h$ and, hence, a constant mean temperature $T_h$ in the bead 20 extremely rapidly. Since the voltage is supplied thereto in a regulated or controlled manner the bead resistance remains substantially constant with time regardless of the heat loss. The potentiometer 22, once it is set, maintains a substantially constant resistance and any changes therein with time are essentially negligible because of the low power and the small temperature coefficient of resistance thereof. The high gain of the control circuitry in FIG. 4 and the excellent frequency response thereof permit the average resistance of the thermistor heater bead to reach the required value, for example, in as little as 10 milliseconds.

Figure 6:
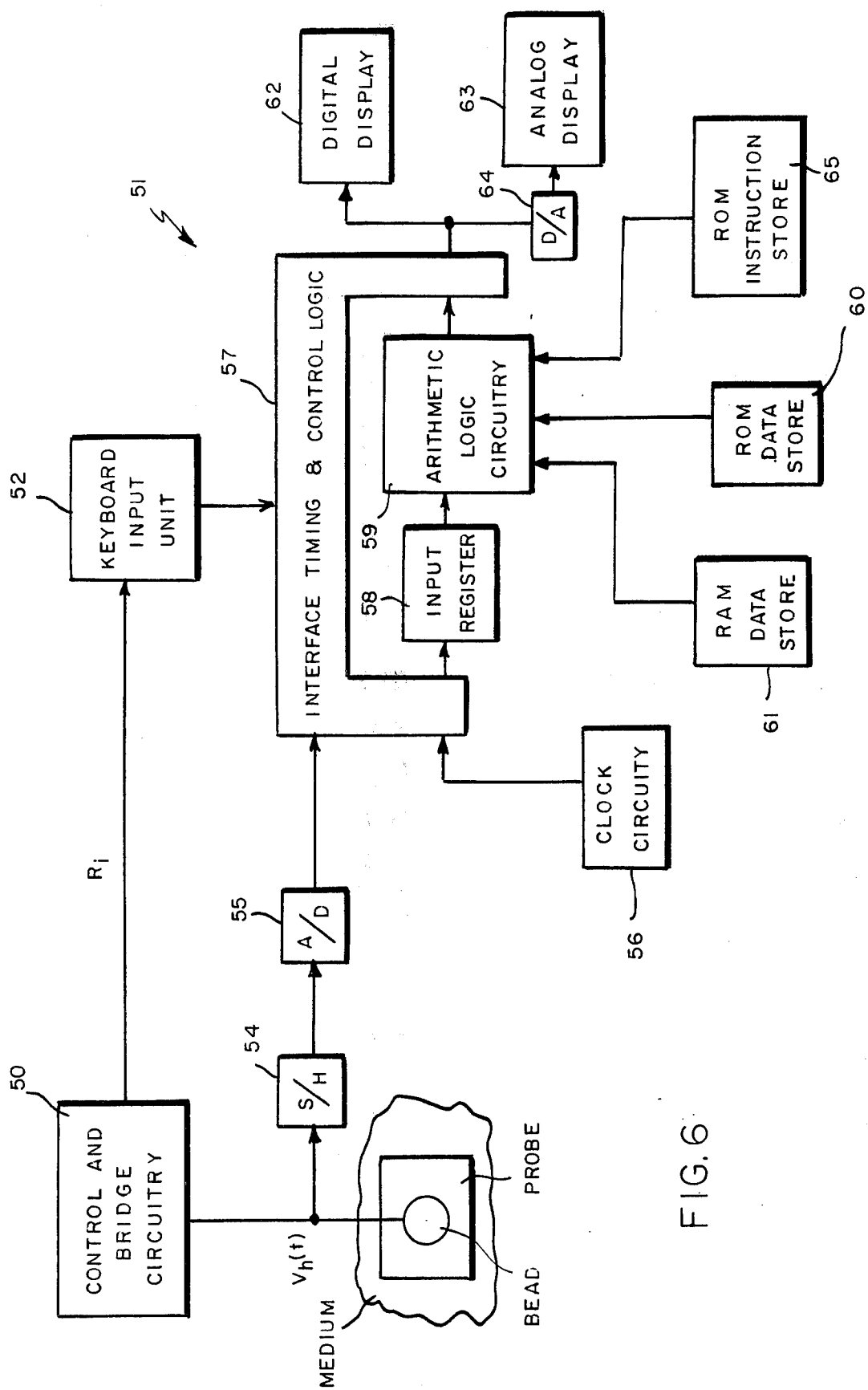
FIG. 6 shows a block diagram of a system for implementing the method of the flow chart of FIG. 5.

The thermal conductivity, $k$, and the thermal diffusivity, $\alpha$, of the medium can be determined using appropriate control circuitry and data processing systems as shown in FIG. 1. Such control circuitry may be either analog or digital, such data processing system may be a large time shared centralized computer, a dedicated mini computer, or a self-contained microprocessor. The following is one implementation of the system using an analog controller and a self-contained microprocessor. As seen in FIG. 6, the control and bridege circuitry 50 (FIG. 4) provides a measure of the resistance $R_i$ which, when so determined, can be stored in a random access memory unit (RAM) 61 via appropriate keyboard input unit 52 in accordance with well-known techniques. The micro processing system 51 includes a read-only-memory unit (ROM) 60 for storing pre-determined data and a (ROM) 65 for storing data handling instructions each of which units operates in a manner well-known to those in the data processing art. The micro processor system further includes an input register 58 of the First In-First Out variety for supplying data to an arithmetic logic unit 59 which also receives data and instructions from the storage units 60, 61 and 65 so that the various calculations described below can be performed. Suitable clock and interface circuitry 56 and 57, respectively, are required to control the transfer of data to and from the micro processor in manners well-known to those in the art. The output data from the data processing system can be appropriately displayed either in digital or analog form at one or more digital and analog display units 62 and 63, respectively, the latter units being supplied with data via a suitable digital-to-analog converter 64. The voltage $V_h(t)$ which is required to determine the thermal conductivity and thermal diffusivity characteristics of the medium is suitably sampled by sample and hold circuitry 54 and analog to digital converter 55 which supply such information to the input register 58 via interface circuitry 57.

Figure 5A:
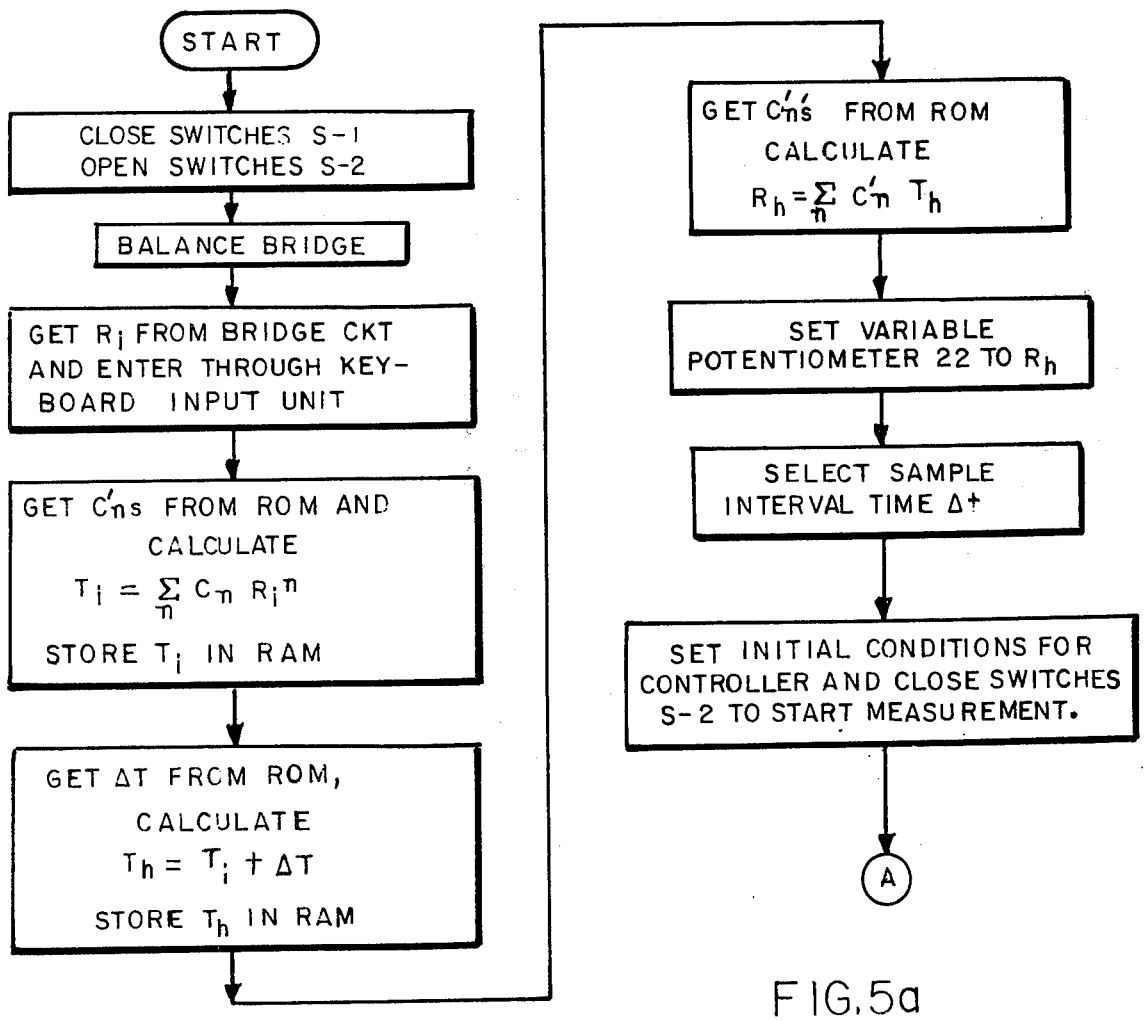
FIGS. 5a and 5b shows a flow chart of the steps performed in accordance with one embodiment of the invention.
Figure 5B:
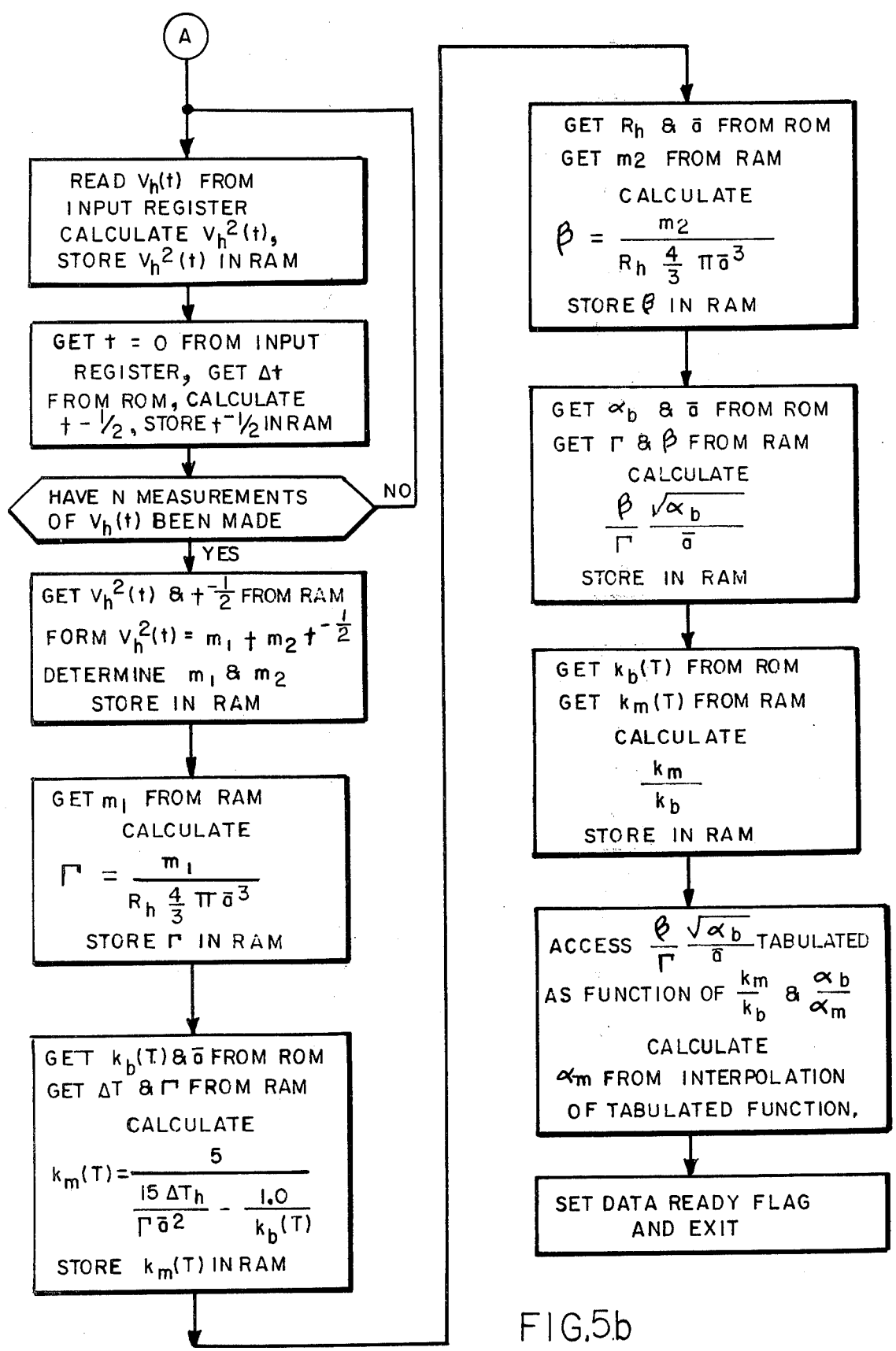
Figure 7:
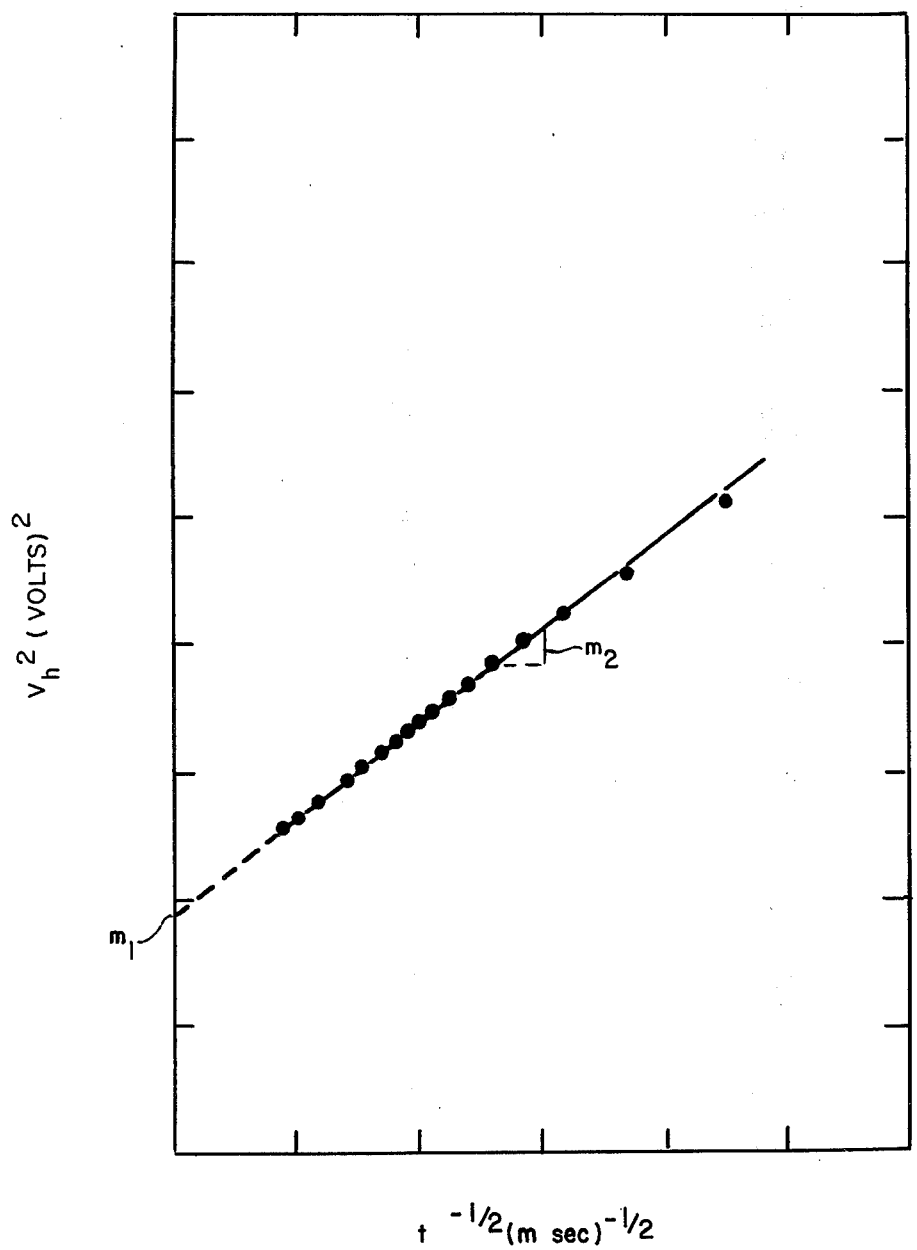
FIG. 7 shows an exemplary and qualitative representative curve used in connection with the method of the flow chart of FIG. 5.

As seen in the flow chart FIG. 5 the initial reference temperature $T_i$ of the bead with a non-heating current applied thereto is first determined as described above from the measurement of $R_i$ and the coefficients $C_n$ stored in the read-only-memory (ROM) unit 60. A voltage $V_h(t)$ is applied to the bead to raise the mean temperature thereof to a value $T_h$ as calculated from a predetermined value of $\Delta T$ also stored in ROM unit 60. The value of the voltage $V_h(t)$ which is so applied is monitored at discrete time intervals during the early time period after application thereof until the voltage level tends to settle to a relatively steady-state value. The values $V_h^2(t)$ (obtained from the monitored values of $V_h(t)$ as a function of the inverse square root of time (i.e., as a function of $t^{-\frac{1}{2}}$), are appropriately obtained at desired equal time intervals $\Delta t$ and appropriately stored in RAM unit 61. Thus, the voltage $V_h(t)$, is applied to the bead and, at a time $t_0$ just after the application thereof, the value $V_h$, thereof is measured and the value $V_h^2(t_0)$ is calculated. At fixed intervals $\Delta t$ of time subsequent thereto (i.e., at $t_1$, $t_2$, $t_3$, . . .) etc., where $t_1-t_0=t_2-t_1=t_3-t_2=\Delta t$) the same measurements of values thereof are performed for $V_h^2(t_1)$, $V_h^2(t_2)$...; etc. at times $t_1$, $t_2$...; etc. The values thereof, as well as the time values are stored in RAM unit 61. The relationship between $V_h^2(t)$ and $t^{-\frac{1}{2}}$ in any media in the absence of free convection is found, for the thermal model used, to be a straight line, as shown by the qualitative exemplary curve depicted in FIG. 7. No specific $V_h^2$ and $t^{-\frac{1}{2}}$ are depicted therein, the actual values thereof in any specific case depending on the particular circumstances and elements used. The intercept $\Gamma$ on the ordinate thereof is a measure of the thermal conductivity while the slope $\beta$ thereof is a measure of the thermal diffusivity. The intercept $\Gamma$ effectively represents the value of the curve at infinite time while $\beta$ effectively represents the slope of the curve over the early time span shortly after $t=0$. The equation of the line in FIG. 7 can be expressed as follows $$V_h^2(t) = m_1 + m_2 t^{-\kappa}$$

The data processor, having the stored values of $V_h^2(t)$ and $t$ in the RAM can thereupon calculate the values of $m_1$ and $m_2$ which satisfy such expression best by using least square linear regression techniques well known in the art. From the calculated value of $m_1$ and the values of $\bar{a}$ and $R_h$, the value of $\Gamma$ can then be calculated in accordance with the following expression $$\Gamma = \frac{m_1}{R_h \frac{4}{3} \pi \bar{a}^3}$$

With the calculated value of $\Gamma$ and the values of $\Delta T$, $a$ and $k_b$ as stored in the ROM unit 60, the thermal conductivity $k$ of the medium can be calculated in accordance with the following expression derived from solutions of the heat conducting equations in accordance with the thermal model discussed above $$K = \frac{5}{\frac{15\Delta T}{\Gamma \bar{a}^2} - \frac{1.0}{K_b}}$$

It should be noted that in the above calculation, $\Delta T$ and $R_h$ are constant. If the above steps are carried out for a medium in which no fluid is flowing the calculated thermal conductivity represents the intrinsic thermal conductivity $k_m$, while if carried out for a medium in which fluid is flowing the thermal conductivity represents the effective thermal conductivity $k_{eff}$.

The calculation of the thermal diffusivity of the medium can then proceed as follows.

In a manner similar to that discussed above, with the calculated value of $m_2$, and the values of $\bar{a}$ and $R_h$, the value of $\beta$ can then be calculated in accordance with the expression $$\beta = \frac{m_2}{R_h \frac{4}{3} \pi \bar{a}^3}$$

Figure 8:
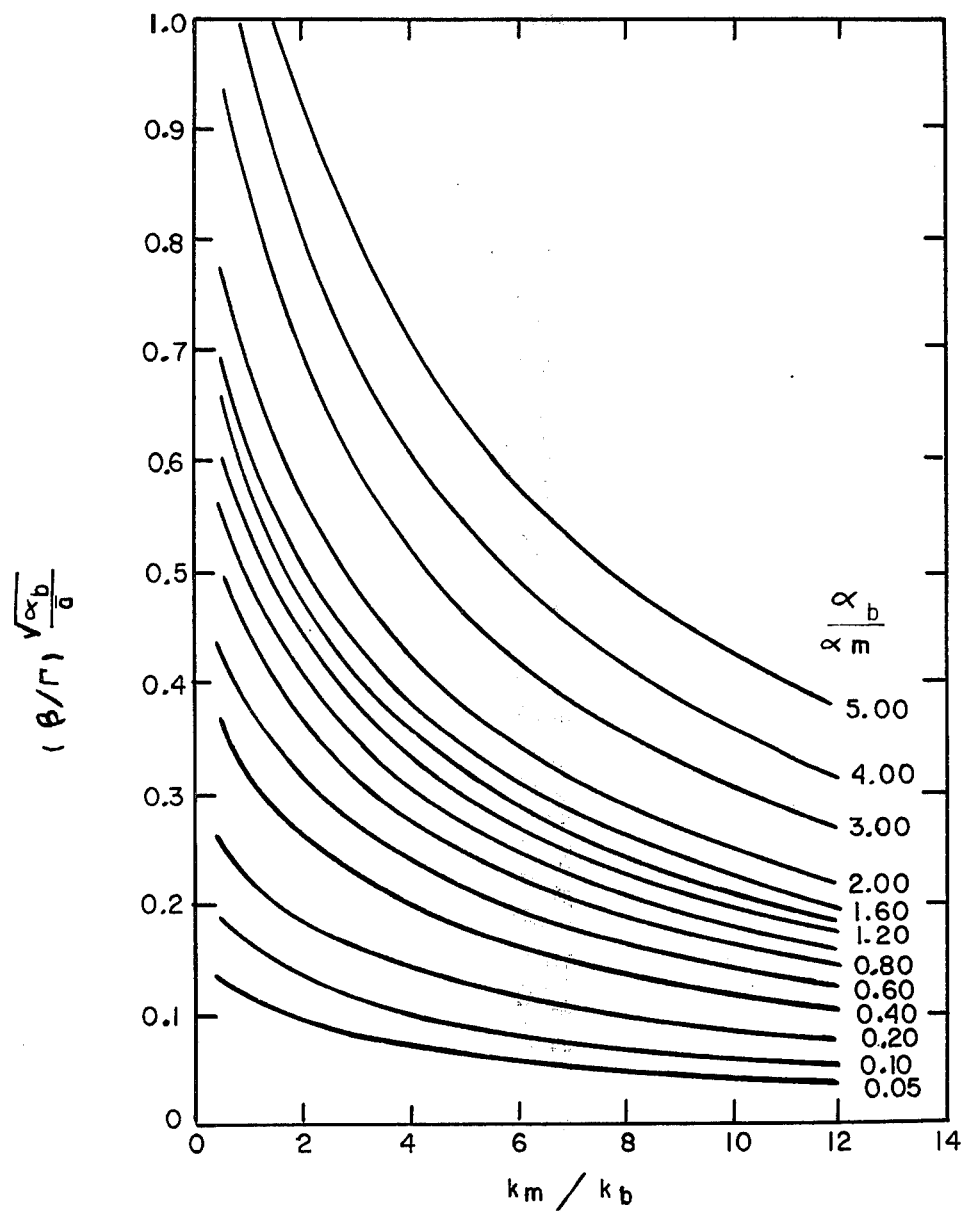
FIG. 8 shows further non-dimensional curves used in connection with the method of the flow chart of FIG. 5.

Based on the above discussed thermal model which has been assumed, general non-dimensional curves, as shown in FIG. 8, can be generated for all media being investigated wherein each such curve is a plot of the quantity $$\frac{\beta}{\Gamma} \cdot \frac{\sqrt{ab}}{\bar{a}} V \cdot \frac{k_m}{k_b}$$

and wherein $\beta$ and $\Gamma$ are as defined above $\alpha_b$ is the known diffusivity of the thermistor bead, which can be predetermined, $k_m$ and $k_b$ are, respectively, the intrinsic thermal conductivities of the medium (determined as previously described above) and the thermal conductivity of the bead (predetermined as discussed above). Each curve is plotted for a particular ratio $\alpha_b/\alpha_m$ of the thermal diffusivities of the bead and the medium. Such non-dimensional curves are generalized ones which apply to all media and can be pre-calculated and the values of the above relationships can be pre-stored in a read-only-memory unit 60 (FIG. 6) in a manner well known in the art.

In order to determine the thermal diffusivity $\alpha_m$ for a particular medium, therefore, $\beta$ and $\Gamma$ are determined experimentally as discussed above. The quantities $\alpha_b$, $\bar{a}$ and $k_b(T)$ are known and are previously stored in the ROM unit 60 and the quantity $k_m(T)$ is determined experimentally and stored in the RAM unit 61 as discussed above. The quantities $$\frac{\beta}{\Gamma} \cdot \frac{\sqrt{ab}}{\bar{a}}$$

and $k_m(T)/k_b(T)$ are calculated by the arithmetic logic unit 59 and the quantity $\alpha_b/\alpha_m$ can be determined from the read-only-memory unit 60 and, since $\alpha_b$ is known, the quantity $\alpha_m$ can be appropriately calculated. Since the ROM unit 60 stores discrete solutions to the relationship of the curves of FIG. 8 appropriate interpolations can be performed by the data processing unit in accordance with techniques known to the data processing art.

The thermal conductivity and thermal diffusivity values which are so determined can be appropriately displayed on display units 62 and 63, as desired.

As mentioned previously, the above process and apparatus for determining the thermal conductivity and thermal diffusivity of a medium can be accomplished over a relatively short time period. However, if a fluid is flowing in a medium, e.g., blood flowing in human tissue, and it is desirable to determine the fluid flow rate $\dot{\omega}$ it is frequently required that the flow rate be determined over a relatively long time period. As mentioned above, over long time periods the reference temperature of the medium may change and the above calculations of the thermal conductivity made while maintaining the heated temperature of the bead at a fixed value produces variations in the temperature difference which must be taken into account.

Hence, preferred methods of determining the effective thermal conductivity (i.e., in the presence of blood flow) require the monitoring of the reference temperature so that the variations in $\Delta T$ can be determined. Accordingly, as shown diagrammatically in FIG. 11, the probe 80 can be fabricated so as to provide two thermistor elements 81 and 82, one used as a temperature sensing element and the other as a heater element. A control and data processing system similar to that described above in FIG. 6 is used in FIG. 11. In this connection provisions are made for sampling the voltages at the sensor bead ($V_s$), the heater bead ($V_h$) and across a fixed resistor $R_f(V_R)$ of the control circuitry via sample and hold circuits 83–85, respectively, the outputs of which are supplied to a multiplexer 86 and, thence, to the data processing system as discussed above which for convenience retains the same reference numerals used in FIG. 6.

If the heated temperature $T_h$ of the bead 81 is determined as in the above described process and is maintained constant at such determined value, the sensor element 82 can provide a measurement of the changes in the reference temperature $T_s$ which occur over a relatively long time period so that the temperature difference $\Delta T$ therebetween, which varies as a function of time, can be recalculated at specified intervals over such a time period.

The values of $k_{eff}$ and $k_m$ can then be re-calculated at each interval in accordance with the following expression wherein it can be noted that the value of $\Delta T$ is a function of time and $R_h$ is constant in contrast to the above described relatively short time measurement technique wherein both $\Delta T$ and $R_h$ are constant:

$$\kappa(t) = \frac{5}{\frac{\Delta T(t) R_h 20\pi \bar{a}}{V_h^2(t)} - \frac{1.0}{\kappa_b}}$$

Such values can then be used to determine the flow rate $\dot{\omega}$ at such intervals of a fluid flowing therein in accordance with the following expression derived from solutions of the heat conduction equations for the thermal model discussed above:

$$\dot{\omega}(t) = \left( \frac{\kappa_{eff}(t)}{\kappa_m(T)} - 1 \right)^2 \frac{\kappa_m(T)}{C_b \bar{a}^2}$$

where $a$ is defined as above and $C_b$ is the heat capacity of the fluid which is flowing in the medium, e.g., the heat capacity of blood in a biologic medium.

Since variations in the temperature difference $\Delta T(t)$ with time tend to affect the flow rate which is being determined, the above method for determining $\omega$ may not provide an accuracy as good as desired. Hence it is preferable to use a method for such determination which maintains the temperature difference $\Delta T$ substantially constant. Such a method would then require that the heated temperature $T_h$ vary with time in a manner so as to follow the variations in the reference temperature $T_s$ measured by the sensing element so that the difference therebetween remains substantially the same. In this way the calculations of the effective thermal conductivity $k_{eff}$ of the medium and the subsequent calculation of the flow rate $\omega$ of a fluid in such medium, which, as shown above, requires the determination of $k_{eff}$, provide more accurate results.

Figure 9:
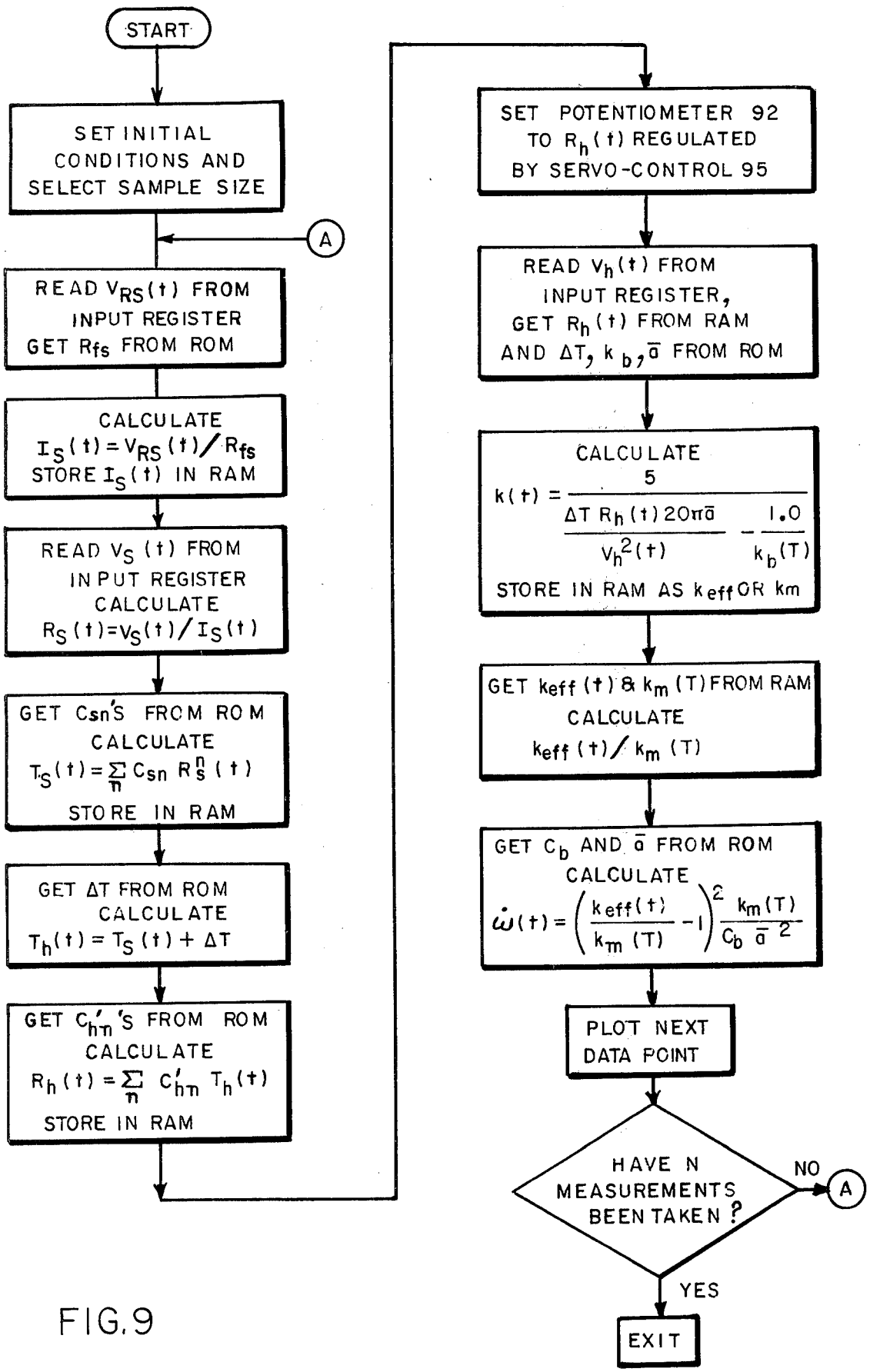
FIG. 9 shows a flow chart of the steps performed in accordance with another embodiment of the invention.
Figure 11:
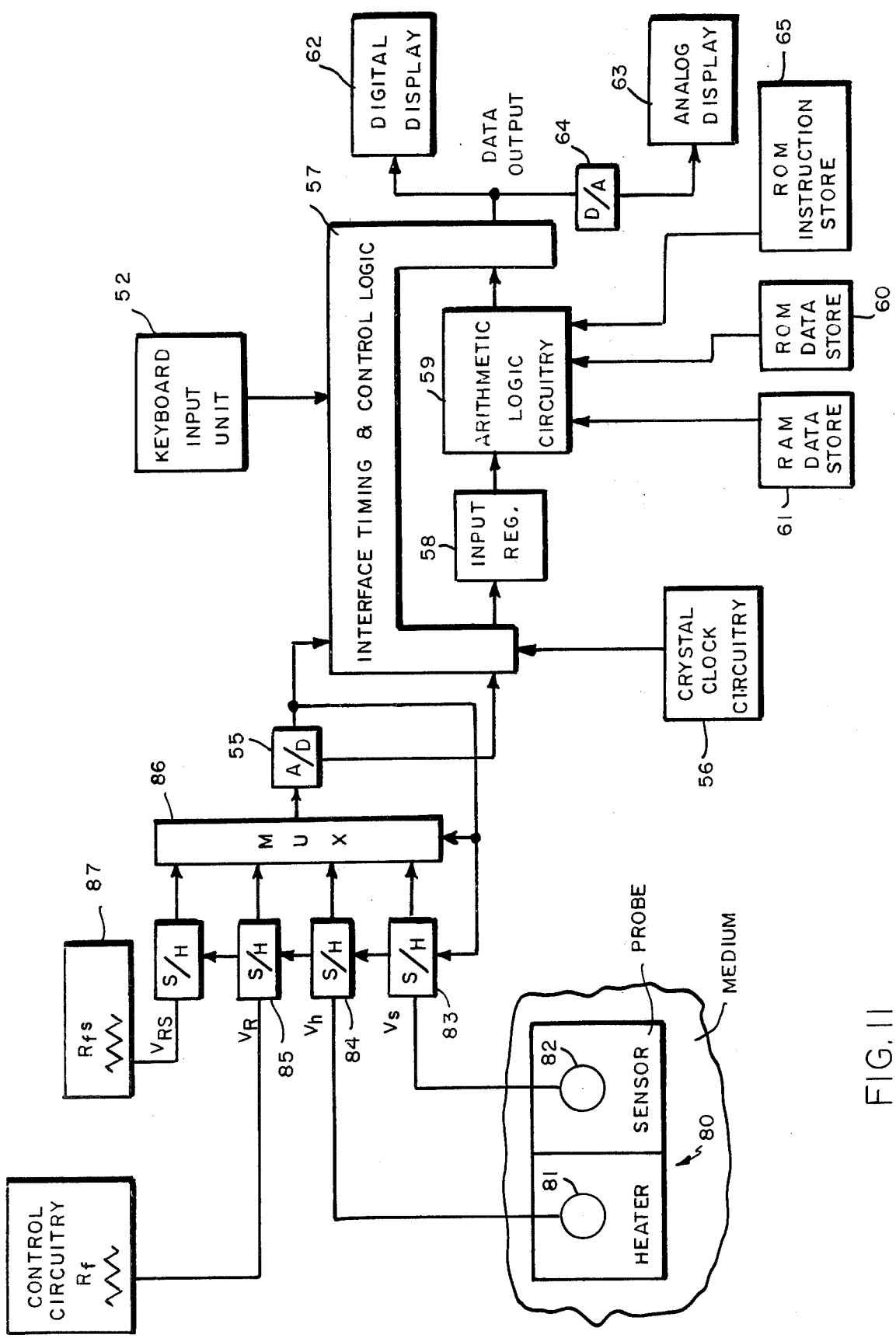
FIG. 11 shows a block diagram of a system which can be used to implement the method of the flow chart of FIG. 9.

The flow chart of FIG. 9 together with the control circuit of FIG. 10A and overall data processing system of FIG. 11, shows an alternative method for calculating the thermal conductivity $k_{eff}(t)$ and $\omega$ wherein the temperature difference $\Delta T$ is kept substantially constant and the heater thermistor resistance $R_h(t)$ varies as a function of time in contrast to the method of FIG. 5 wherein the heater thermistor resistance $R_h$ remains substantially constant over the short time measurement involved therein. The control circuit of FIG. 10A, in the same manner as that shown in FIG. 4, uses a two stage operational amplifier configuration and, unlike FIG. 4, the operational amplifiers are connected to a series combination of a thermistor heater bead 90, a variable potentiometer 92 and a pair of fixed resistors 91 and 93 each having a fixed value $R_f$. As seen in FIG. 11, the sensing thermistor bead has a fixed resistor 87 having a resistance $R_{fs}$ also in series therewith, as shown more specifically in the overall sensor circuitry of FIG. 10B, and, in order to determine the temperature $T_s$ thereof, the voltage $V_{Rs}$ is measured across $R_{fs}$ and the current $I_s$ therethrough is calculated. The voltage $V_s(t)$ across the sensor bead is then measured and the resistance $R_s(t)$ thereof calculated. The coefficients $C_{sn}$ previously stored in the ROM unit are then used to calculate the temperature $T_s(t)$ of the sensor bead in accordance with the expression $$T_s(t) = \sum_n C_{sn} R_s^n(t)$$

The predetermined constant temperature difference $\Delta T$ which is previously stored in the ROM unit is used to calculate the desired heater bead temperature $T_h(t)$ in accordance with the expression $$T_h(t) = T_s(t) + \Delta T$$

From such calculation a further calculation of the heater bead resistance $R_h(t)$ is made and stored in the RAM unit from appropriate coefficients $C_{hn}$'s previously stored in the ROM unit in accordance with the expression $$R_h(t) = \sum_n C_{hn} T_h^n(t).$$

The resistance of the variable potentiometer is automatically set to the calculated value of the resistance $R_h$ by the control circuit of FIG. 10A. Thus, the current through potentiometer 92 is determined by measuring the voltage across fixed resistor 93 having a known value $R_f'$ and the resistance $R_p$ of potentiometer determined by measuring the voltage $V_{RP}$ thereacross and calculating $R_p$ from the previously calculated current therethrough. $R_p$ is compared with the previously calculated desired resistance $R_h$ in an appropriate servo-control circuit 95 for changing the value $R_p$ until the difference between $R_p$ and $R_h$ is zero. When the value $R_p$ is so maintained the value of the voltage applied across the series resistance arrangement is such that the actual resistance $R_h(t)$ of the heater bead 90 is maintained at a value which follows the desired value thereof as set on potentiometer 92 as discussed above with reference to the control circuit of FIG. 4.

The volage $V_h(t)$ required to maintain $\Delta T$ constant is obtained from the control circuit and supplied to the input register 58 as shown in FIG. 11. With such value and the values of $R_h(t)$ and $\Delta T$ stored in the RAM and ROM units, respectively, together with the known values of $k_b(T)$ and $\bar{a}$ previously stored in ROM unit 60, a calculation of the thermal conductivity $k(t)$ is made at a given temperature level $T_h$ in accordance with the expression $$\kappa(t) = \frac{5}{\dfrac{\Delta T\, R_h(t)\, 20\pi \bar{a}}{V_h^2(t)} - \dfrac{1.0}{\kappa_b(T)}}$$

in which it can be seen that $\Delta T$ is constant and $R_h(t)$ varies as a function of time in contrast to the previously used expression for $k(t)$ wherein $\Delta T$ and $R_h$ are both constant or wherein $\Delta T$ is a function of time and $R_h$ is constant. Such calculation will represent either $k_{eff}(t)$ or $k_m(t)$ depending on whether a fluid is or is not flowing in the medium. Appropriate calculation of $\omega$ can then be made once $k_{eff}(T,t)$ and $k_m(T)$ are determined.

Thus with the calculated values of $k_{eff}(t)$ and $k_m(T)$, together with the previously stored values of $C_b$ (i.e., the known heat capacity of the fluid which, for example, may be the known heat capacity of blood) and $\bar{a}$ a calculation of $\omega(t)$ can be made in accordance with the expression $$\dot{\omega}(t) = \left(\frac{\kappa_{eff}(t)}{\kappa_m(t)} - 1\right)^2 \frac{\kappa_m(t)}{C_b\, \bar{a}^2},$$

which expression is derived from the solutions of the heat conduction equation in accordance with the thermal model discussed above.

Another implementation for providing constant $\Delta T$ would be an effective digital circuit as shown in FIG. 12 which would replace the circuit shown in FIG. 10A. In FIG. 12 the feedback logs for controlling $\Delta T$ and $R_h$ is closed through the data processor itself. The system block diagram of FIG. 11 and the method of measuring sensor temperature as shown in FIG. 10B remain unchanged. Thus, the data processor supplies a digital voltage, which is converted to analog form by a suitable digital to analog (DA) converter and applied across the series combination of fixed resistor $R_f$ and the heater element resistance $R_h$. The voltage $V_f$ across the fixed resistance $R_f$ is appropriately measured and supplied to the data processor in digital form via a suitable AD converter. From such measurements the voltage across and the current through the heater element can be calculated and the actual resistance $R_h$ of the heater element determined. The value of $R_h$ which is so determined is compared with the desired value of $R_h$ and the voltage supplied by the data processor is varied until the difference between the measured value of $R_h$ and the desired value of $R_h$ is effectively reduced to zero, so that the actual value of $R_h$ is maintained at the desired value thereof.

Figure 13:
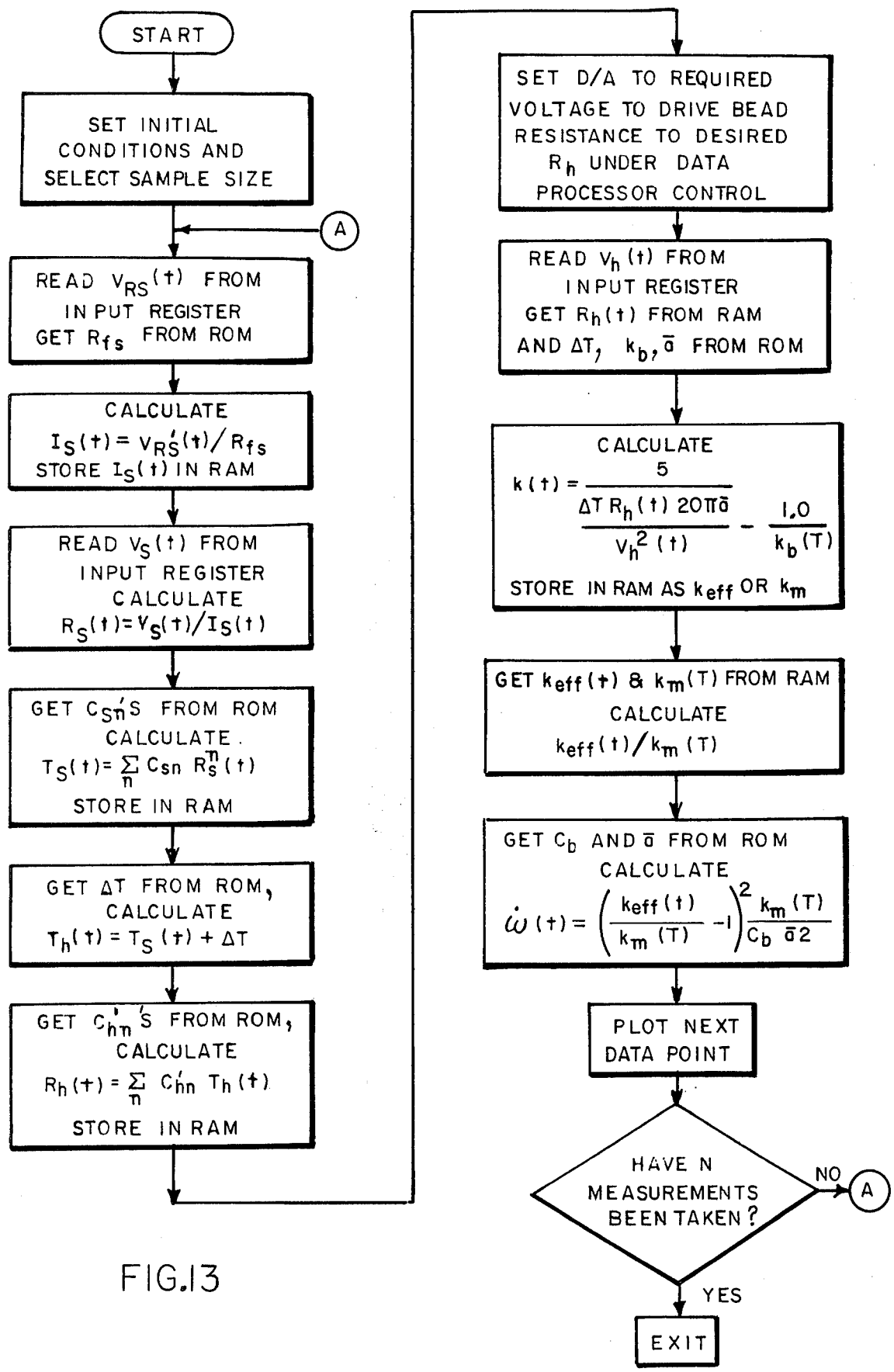
FIG. 13 shows a flow chart of an alternative method of the invention with reference to the control circuit of FIG. 12.

A flow chart showing the method of determining $k(t)$ and $\omega(t)$ is shown in FIG. 13 which differs from the flow chart depicted in FIG. 9 only in the manner in which $R_h$ is controlled in accordance with the control circuit of FIG. 12.

Figure 14:
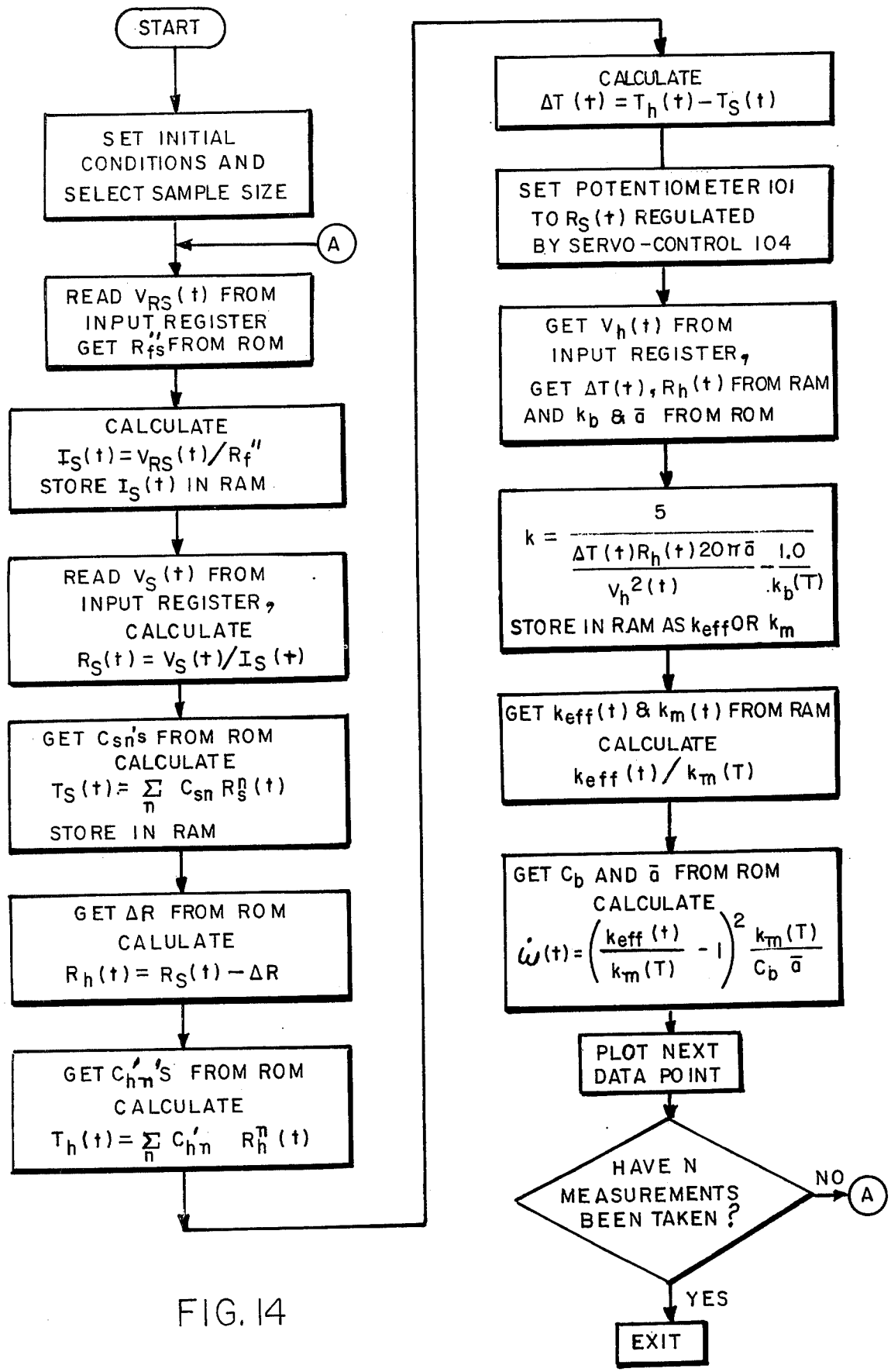
FIG. 14 shows a flow chart of still another alternative method of the invention.

Alternatively, the system of FIGS. 9-13 may be arranged to provide the desired measurements of $k(t)$ and $\omega(t)$ in a manner in which the resistance difference, $\Delta R$, between the resistances of the sensor thermistor element and the heater thermistor element is maintained at a substantially constant value rather than the temperature difference $\Delta T$ therebetween. As can be seen from the flow chart of FIG. 14, and the control circuit of FIG. 15 the calculation of the reference sensor resistance and temperature $T_s(t)$ is the same as that shown in FIG. 9 and the predetermined $\Delta R$ is obtained from the ROM unit in which it has been previously stored. The desired heater element resistance $R_h(t)$ is thereupon determined as $$R_h(t) = R_2(t) - \Delta R.$$

From such calculation the desired heater element temperature $T_h(t)$ is calculated as previously discussed and the temperature difference $\Delta T(t)$ is calculated. Since the sensor element resistance $R_s(t)$ varies as a function of time over the relatively long time period involved, the desired heater element resistance $R_h(t)$ and the temperature difference $\Delta T(t)$ both vary with time in the expression for the thermal conductivity in contrast to the above described short time and long time methods for calculating such quantity $$\kappa(t) = \cfrac{5}{\cfrac{\Delta T(t) \, R_h(t) \, 20\pi\bar{a}}{V^2_h(t)} - \cfrac{1.0}{\kappa_b}}$$

The value of $\dot\omega$ is then calculated as above, all of the above calculations utilizing a data processing system of the type shown in FIG. 11.

The control circuit for maintaining the resistance difference $\Delta R$ substantially constant is shown in FIG. 15 which utilizes a form substantially similar to those shown with reference to FIGS. 4 and 10A.

As can be seen in FIG. 15, a series resistance arrangement used therein comprises a fixed resistance 100 having a fixed value $R_f''$, a variable potentiometer 101 having a variable resistance $R_p'$, a fixed resistance 102 having a value of $R_f'' + \Delta R$ and the heater element 103 having a resistance $R_h$. Once the desired value of $R_s$ is calculated as shown by the flow chart of FIG. 14, the variable potentiometer is set at the value of $R_s$ and maintained thereat in the same manner as discussed above in FIG. 10A for maintaining the variable resistance at $R_h$. As can be seen, the control circuit maintains the voltage at the junction point 105 at zero value so that $$R_f'' + R_s + R_f'' + \Delta R + R_h.$$

Thus, the selected constant resistance difference is maintained as calculated from the known value of $\Delta R$. The value of $R_p$ is then suitably set to the desired $R_s$ value in the same manner as before and the value of the heater bead resistance is automatically set by the overall control circuitry as before.

The systems and processes depicted in FIGS. 9-15 provide substantially continuous long time determinations of the effective thermal conductivities $k_{eff}(t)$ of a medium in which a fluid is flowing and of the flow rate $\omega(t)$ of such fluid, which quantities can be appropriately displayed either temporarily or in permanently recorded forms as desired.

The overall circuitry, probes and display devices for all of the techniques described above for determining and displaying thermal conductivity, thermal diffusivity and flow rate can be fabricated as a relatively small and portable apparatus which can be conveniently used by an operator at a variety of locations.

What is claimed is:

1. A method for determining physical characteristics of a medium comprising the steps of
   predetermining the thermal conductivity of a heating means as a function of temperature, said heating means having a predetermined resistance versus temperature relationship;
   immersing said heating means in said medium;
   determining the reference temperature of said medium when said medium is unheated;
   applying power to said heating means sufficiently rapidly to heat said means to a volume mean temperature above said reference temperature so that the power necessary to maintain said volume mean temperature varies as a function of time;
   determining the time varying relationship between the power required to maintain said heating means at said volume mean temperature after said temperature has been reached and the time during which said power is being applied thereto;
   determining the temperature difference between said volume mean temperature and said reference temperature and determining the resistance of said heating means at said volume mean temperature;
   determining the thermal conductivity of said medium as a function of said temperature difference, of the resistance of said heating means at said volume mean temperature, of said applied power in accordance with said time varying power and time relationship, of said predetermined thermal conductivity of said heating means, and of at least one characteristic dimension of said heating means in accordance with a thermal model of said heating means and said medium in which it is immersed wherein said heating means is treated as a distributed thermal mass and wherein heat conduction occurs in a coupled thermal system which comprises both the heating means and the adjacent region of said medium which surrounds said heating means.

2. A method in accordance with claim 1 wherein said reference temperature is determined over a relatively short time period over which it remains substantially constant and further including the steps of
   maintaining said volume mean temperature at a fixed, predetermined value above said reference temperature, said time varying power and time relationship being determined in terms of the relationship between the square of the voltage applied to said heating means and the inverse square root of the time during which said voltage is being applied;

determining a first characteristic $\Gamma$ of said relationship representing the value of the power per unit volume generated by the heating means at a time $t$ effectively equivalent to an infinite time period following the application of said power to said heating means;

and further wherein said thermal conductivity of said medium is determined in accordance with the expression:

$$k = \frac{5}{\frac{15\Delta T}{\Gamma \bar{a}^2} - \frac{1.0}{k_b(T)}}$$

where $k$ is the thermal conductivity of said medium, $\Delta T$ is the said fixed volume mean temperature difference, $\bar{a}$ is the radius of a spherical heating means having a volume equivalent to the actual volume of said heating means, and $k_b$ is said predetermined thermal conductivity of said heating means.

3. A method in accordance with claim 2 wherein the step of determining said reference temperature includes the steps of
measuring the voltage at said heating means in its unheated state;
determining the current through said heating means in its unheated state;
determining the resistance of said heating means in its unheated state; and
determining said reference temperature in accordance with the said predetermined resistance versus temperature relationship of said heating means.

4. A method in accordance with claim 3 wherein the step of maintaining said volume mean temperature at said fixed value further includes the steps of
preselecting a fixed value for said temperature difference;
determining said volume mean temperature from said reference temperature and said preselected fixed temperature difference;
determining the resistance of said heating means at said volume mean temperature in accordance with said predetermined resistance versus temperature relationship; and
maintaining the resistance of said heating means at a substantially constant value equal to said determined resistance whereby said volume mean temperature remains at a substantially constant value.

5. A method in accordance with claim 2 wherein said time varying relationship between the square of the voltage $V_h^2$ and the inverse square root of the time $t^{-\frac{1}{2}}$ is a substantially linear relationship of the form $V_h^2(t) = m_1 + m_2 t^{-\frac{1}{2}}$;

and further wherein said first characteristic $\Gamma$ is determined in accordance with the expression:

$$\Gamma = \frac{m_1}{R_h \frac{4}{3} \pi \bar{a}^3}$$

6. A method in accordance with claim 2 and further including the steps of
predetermining the thermal diffusivity of said heating means;
determining a second characteristic $\beta$ representing the slope of the time varying relationship between the square of the voltage $v_h^2$ and the inverse square root of the time $t^{-\frac{1}{2}}$ at a time relatively shortly after the time at which said power is applied;
predetermining the non-dimensional relationship between the expression $\beta \sqrt{a_b} / \Gamma \bar{a}$ wherein $a_b$ is the predetermined thermal diffusivity of said heating means; the expression $k_m/k_b$, wherein $k_m$ is the thermal conductivity of said medium with no fluid flowing therein; and the expression $a_b/a_m$ where $a_m$ is thermal diffusivity of any medium which is to be determined;
determining the actual value of $\beta \sqrt{a_b} / \Gamma \bar{a}$ and $k_m/k_b$ at said volume mean temperature and further determining the value of $a_b/a_m$ in accordance with said predetermined non-dimensional relationship; and
determining the thermal diffusivity $a_m$ of said medium in accordance with the determined value of $a_b/a_m$.

7. A method in accordance with claim 6 wherein said time varying relationship between the square of the voltage $V_h^2$ and the inverse square root of time $t^{-\frac{1}{2}}$ is a substantially linear relationship of the form $V_h^2(t) = m_1 + m_2 t^{-\frac{1}{2}}$;

and further wherein said first characteristic $\Gamma$ is determined in accordance with the expression:

$$\Gamma = \frac{m_1}{R_h \frac{4}{3} \pi \bar{a}^3} \text{; and}$$

said second characteristic $\beta$ is determined in accordance with the expression:

$$\beta = \frac{m_2}{R_h \frac{4}{3} \pi \bar{a}^3}.$$

8. A method in accordance with claim 1 wherein said reference temperature varies with time over a relatively long time period and further including the steps of
determining said reference temperature value over said time period;
maintaining said volume mean temperature at a fixed, predetermined value, said fixed value being greater than said reference temperature over said time period;
determining the time-varying temperature difference between said fixed volume mean temperature and said time-varying reference temperature;
determining the fixed value of the resistance of said heating means at said volume mean temperature; and
determining the thermal conductivity of said medium over said time period in accordance with the expression $$k(t) = \frac{5}{\frac{\Delta T(t) R_h 20\pi \bar{a}}{V_h^2(t)} - \frac{1.0}{k_b(T)}}$$

where $k(t)$ is the thermal conductivity of said medium, $\Delta T$ is said temperature difference, $R_h$ is the said fixed resistance of said heating means at said volume mean temperature, $a$ is the radius of a spherical heating means having a volume equivalent to the actual volume of said heating means, $V_h(t)$ is the voltage at said heating means where said power is applied, and $k_b$ is said predetermined thermal conductivity of said heating means.

9. A method in accordance with claim 8 wherein the step of determining said reference temperature includes the steps of immersing a temperature sensing means in said medium at a region sufficiently remote from the immersed heating means so that the temperature sensed by said sensing element is not affected by the raised temperature of said heating means, said sensing means having a predetermined resistance versus temperature relationship;

determining over said time period the voltage at said sensing means and the current through said sensing means;

determining the reference temperature sensed by said sensing means over said time period in accordance with the said predetermined resistance versus temperature relationship thereof.

10. A method in accordance with claim 9 wherein the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium;

and further including the steps of predetermining the heat capacity $C_b$ of said fluid;

determining the ratio of $k_{eff}(t)/k_m$ over said time period; and determining the rate of flow $\dot{\omega}(t)$ of said fluid in said medium in accordance with the expression:

$$\dot{\omega}(t) = \left(\frac{k_{eff}(t)}{k_m} - 1\right)^2 \frac{k_m}{C_b \bar{a}^2}$$

where $\omega(t)$ is measured in terms of the mass of fluid per unit volume of the medium per unit time.

11. A method in accordance with claim 1 wherein said reference temperature varies with time over a relatively long time period and further including the steps of determining said reference temperature over said time period;

determining the said volume mean temperature over said time period as a function of said reference temperature and a preselected fixed value of said temperature difference;

maintaining the resistance of said heating means over said time period at a value such as to maintain the temperature difference between said volume mean temperature and said reference temperature at said preselected fixed value, said resistance varying as a function of time;

determining the thermal conductivity $k(t)$ of said medium over said time period in accordance with the expression:

$$k(t) = \cfrac{5}{\cfrac{\Delta T\, R_h(t)\, 20\pi\bar{a}}{V_h^2(t)} - \cfrac{1.0}{k_b(T)}}$$

where $\Delta T$ is said temperature difference, $R_h(t)$ is said resistance of said heating means at said volume mean temperature, $\bar{a}$ is the radius of a spherical heating means having a volume equivalent to the actual volume of said heating means, $V_h(t)$ is the voltage at said heating means when said power is applied and $k_b$ is the predetermined thermal conductivity of said heating means.

12. A method in accordance with claim 11 wherein the step of determining said reference temperature includes the steps of immersing a temperature sensing means in said medium at a region sufficiently remote from the immersed heating means so that the temperature sensed by said sensing element is not affected by the raised temperature of said heating means, said sensing means having a predetermined resistance versus temperature relationship;

determining over said time period the voltage at said sensing means and the current through said sensing means;

determining the reference temperature sensed by said sensing means over said time period in accordance with the said predetermined resistance versus temperature relationship thereof.

13. A method in accordance with claim 12 wherein the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium;

and further including the steps of predetermining the heat capacity $C_b$ of said fluid;

determining the ratio of $k_{eff}(t)/k_m$ over said time period; and determining the rate of flow $\dot{\omega}(t)$ of said fluid in said medium in accordance with the expression:

$$\dot{\omega}(t) = \left(\frac{k_{eff}(t)}{k_m} - 1\right)^2 \frac{k_m}{C_b \bar{a}^2}$$

where $\dot{\omega}(t)$ is measured in terms of the mass of the fluid per unit volume of the medium per unit time.

14. A method in accordance with claim 1 wherein said reference temperature varies with time over a relatively long time period and further including the steps of immersing a temperature sensing means in said medium at a region sufficiently remote from the immersed heating means so that the temperature sensed by said sensing element is not affected by the raised temperature of said heating means, said sensing means having a predetermined resistance versus temperature relationship;

determining the resistance of said sensing means over said time period;

determining the reference temperature of said sensing means over said time period;

determining the desired resistance of said heating means over said time period as a function of the resistance of said sensing means and of a preselected fixed value of the resistance difference between the resistances of said sensing means and said heating means;

maintaining the resistance of said heating means at said desired resistance value over said time period so that said resistance difference remains at said preselected fixed value, the resistance of said heating means varying as a function of time;

determining the mean temperature of said heating means over said time period at the said desired resistance value of said heating means, said mean temperature varying as a function of time;

determining the temperature difference between said mean temperature and said reference temperature over said time period, said temperature difference varying as a function of time;

determining the thermal conductivity $k(t)$ of said medium over said time period in accordance with the expression;

$$kt = \frac{5}{\frac{\Delta T(t) R_h(t) 20\pi\bar{a}}{V_h^2(t)} - \frac{1.0}{k_b(T)}}$$

where $\Delta T(t)$ is said temperature difference, $R_h(t)$ is said resistance of said heating means at said mean temperature, $\bar{a}$ is the radius of a spherical heating means having a volume equivalent to the actual volume of said heating means, $V_h(t)$ is the voltage at said heating means when said power is applied and $k_b$ is the predetermined thermal conductivity of said heating means.

15. A method in accordance with claim 14 wherein the step of determining said reference temperature includes the steps of immersing a temperature sensing means in said medium at a region sufficiently remote from the immersed heating means to that the temperature sensed by said sensing element is not affected by the raised temperature of said heating means, said sensing means having a predetermined resistance versus temperature relationship;

determining over said time period the voltage at said sensing means and the current through said sensing means;

determining the reference temperature sensed by said sensing means over said time period in accordance with the said predetermined resistance versus temperature relationship thereof.

16. A method in accordance with claim 15 wherein the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium;

and further including the steps of predetermining the heat capacity $C_b$ of said fluid;

determining the ratio of $k_{eff}(t)/k_m$ over said time period; and determining the rate of flow of said fluid in said medium in accordance with the expression:

$$\dot{\omega}(t) = \left(\frac{k_{eff}(t)}{k_m} - 1\right)^2 \frac{k_m}{C_b \bar{a}^2}$$

where $\dot{\omega}(t)$ is measured in terms of the mass of the fluid per unit volume of medium per unit time.

17. Apparatus for determining physical characteristics of a medium comprising means immersed in said medium for sensing the reference temperature of said medium when said medium is unheated;

means immersed in said medium for heating said medium, said heating means having a predetermined thermal conductivity, a predetermined thermal diffusivity and a predetermined characteristic dimension;

means for applying power to said heating means sufficiently rapidly to raise the temperature of said heating means to a volume mean temperature above said reference temperature so that the power necessary to maintain said volume mean temperature varies as a function of time;

data processing means for determining the temperature difference between said volume mean temperature and said reference temperature, for determining the resistance of said heating means at said volume mean temperature and for determining the time varying relationship between the power required to maintain said heating means at said volume mean temperature after said temperature has been reached and the time during which said power is being applied thereto;

said data processing means further being responsive to said temperature difference, said heating means resistance, said applied power in accordance with said time varying power and time relationship, said predetermined thermal conductivity of said heating means, and said predetermined characteristic dimension of said heating means for determining the thermal conductivity of said medium in accordance with a thermal model of said heating means and said medium wherein said heating means is treated as a distributed thermal mass and wherein heat conduction occurs in a coupled thermal system which comprises both the heating means and the adjacent region of said medium which surrounds said heating means.

18. Apparatus in accordance with claim 17 wherein said sensing means and said heating means comprises a single element capable of sensing the temperature of said medium and of heating said medium.

19. Apparatus in accordance with claim 18 wherein said single element is a thermistor bead element.

20. Apparatus in accordance with claim 18 and further including volume means for maintaining said mean temperature at a fixed, predetermined value above said reference temperature, said reference temperature being determined and said volume mean temperature being maintained over a relatively short time interval during which said reference temperature remains substantially constant whereby said temperature difference and the resistance of said heating means also remain substantially constant.

21. Apparatus in accordance with claim 20 and said data processing means further includes means for determining said time varying power and time relationship in terms of the relationship between the square of the voltage applied to said heating means and the inverse square root of the time during which said voltage is being applied;

means for determining a first characteristic $\Gamma$ of said relationship representing the value of the power per unit volume generated by the heating means at a time t effectively equivalent to an infinite time period following the application of said power to said heating means; and means for determining the thermal conductivity of said medium in accordance with the expression:

$$k = \cfrac{5}{\cfrac{15\Delta T}{\Gamma \bar{a}^2} - \cfrac{1.0}{k_b(T)}}$$

where $k$ is said thermal conductivity of said medium, $\Delta T$ is said mean temperature difference, $\bar{a}$ is the radius of a spherical heating means having a volume equivalent to the actual volume of said heating means and $k_b$ is said predetermined thermal conductivity of said heating means.

22. Apparatus in accordance with claim 21 wherein said time varying relationship
between the square of the voltage $V_h^2$ and the inverse square root of the time $t^{-\frac{1}{2}}$ is a substantially linear relationship of the form $V_h^2(t) = m_1 + m_2 t^{-\frac{1}{2}}$; and
said first characteristic determining means includes means for determining said first characteristic $\Gamma$ in accordance with the expression $$\Gamma = \frac{m_1}{R_h \frac{4}{3} \pi \bar{a}^3}$$

where $R_h$ is the resistance of said heating means at said volume mean temperature.

23. Apparatus in accordance with claim 22 wherein said data processing system further includes
means for determining a second characteristic $\beta$ in accordance with the expression:

$$\beta = \frac{m_2}{R_h \frac{4}{3} \pi \bar{a}^3} \text{ ; and}$$

memory storage means for storing the non-dimensional predeterminable relationship between the expression $\beta \sqrt{\alpha_b / \Gamma \bar{a}}$ wherein $\alpha_b$ is the predetermined thermal diffusivity of said heating means; the expression $k_m/k_b$, wherein $k_m$ is the thermal conductivity of said medium with no fluid flowing therein; and the expression $\alpha_b/\alpha_m$ is the thermal diffusivity of any medium which is to be determined; and
means for determining the actual value of said expression $\beta \sqrt{\alpha_b/\Gamma \bar{a}}$ and $k_m/k_b$ and for determining the actual value of $\alpha_b/\alpha_m$ from said memory storage means; and
means responsive to the value of $\alpha_b/\alpha_m$ for determining the thermal diffusivity $\alpha_m$ of said medium.

24. Apparatus in accordance with claim 17 wherein said sensing means and said heating means comprise
a first heating element immersed at a first region of said medium; and
a second element immersed at a second region of said medium sufficiently remote from said first region as to be not affected by the heating of said first element.

25. Apparatus in accordance with claim 24 wherein said first and second elements are thermistor bead elements.

26. Apparatus in accordance with claim 24 for use over a relatively long time period during which said reference temperature varies with time and wherein
said second element determines said reference temperature over said time period; and further including
means for maintaining said volume mean temperature and the resistance of said heating means at said volume mean temperature at fixed predetermined values over said time period during which said reference temperature varies whereby the temperature difference therebetween varies over said time period.

27. Apparatus in accordance with claim 26 wherein said data processing means determines the thermal conductivity of said medium over said time period in accordance with the expression:

$$k(t) = \cfrac{5}{\cfrac{\Delta T(t) R_h 20\pi \bar{a}}{V_h^2(t)} - \cfrac{1.0}{k_b(T)}}$$

where $k(t)$ is said thermal conductivity, $\Delta T(t)$ is said temperature difference, $R_h$ is the resistance of said heating means at said mean temperature, $V_h(t)$ is the voltage at said heating means as power is applied thereto, $\bar{a}$ is the radius of a spherical heating means having a volume equivalent to the actual volume of said heating means and $k_b$ is said predetermined thermal conductivity of said heating means.

28. Apparatus in accordance with claim 27 wherein said date processing system includes
means for determining the intrinsic thermal conductivity $k_m$ of said medium when no fluid is flowing therein;
means for determining the effective thermal conductivity $k_{eff}(t)$ of said medium when a fluid having a predetermined heat capacity is flowing therein;
means for determining the ratio of $k_{eff}(t)/k_m$ over said time period; and
means for determining the rate of flow $\dot{\omega}(t)$ of said fluid in said medium in accordance with the expression:

$$\dot{\omega}(t) = \left( \frac{k_{eff}(t)}{k_m} - 1 \right)^2 \frac{k_m}{C_b \bar{a}^2}$$

where $C_b$ is said predetermined heat capacity.

29. Apparatus in accordance with claim 24 and for use over a relatively long time period during which said reference temperature varies with time wherein
said second element determines said reference temperature over said time period; and further including
means for determining the said volume mean temperature over said time period as a function of said reference temperature and a preselected fixed value of said temperature difference;
means for maintaining the resistance of said first element over said time period at a value such as to maintain the temperature difference between said volume mean temperature and said reference temperature at said preselected fixed value, said resistance varying as a function of time; and
means for determining the thermal conductivity of said medium over said time period in accordance with the expression:

$$k(t) = \cfrac{5}{\cfrac{\Delta T R_h(t) 20\pi \bar{a}}{V_h^2(t)} - \cfrac{1.0}{k_b(T)}}$$

where $\Delta T$ is said temperature difference, $R_h(t)$ is said resistance of said heating means at said volume mean temperature, $\bar{a}$ is the radius of a spherical heating means having a volume equivalent to the actual volume of said first element, $V_h(t)$ is the voltage at said first element when power is applied thereto, and $k_b$ is the predetermined thermal conductivity of said first element.

30. Apparatus in accordance with claim 29 wherein said data processing system includes means for determining the intrinsic thermal conductivity $k_m$ of said medium when no fluid is flowing therein;

means for determining the effective thermal conductivity $k_{eff}(t)$ of said medium when a fluid having a predetermined heat capacity is flowing therein;

means for determining the ratio of $k_{eff}(t)/k_m$ over said time period; and means for determining the rate of flow $\dot{\omega}(t)$ of said fluid in said medium in accordance with the expression:

$$\dot{\omega}(t) = \left( \frac{k_{eff}(t)}{k_m} - 1 \right)^2 \frac{k_m}{C_b \bar{a}^2}$$

where $C_b$ is said predetermined heat capacity.

31. Apparatus in accordance with claim 24 for use over a relatively long time period during which said reference temperature varies with time wherein said second element determines said reference temperature over said time period; and further including means for determining the resistance of said second element over said time period;

means for determining the desired resistance of said first element over said time period as a function of the resistance of said second element and of a preselected fixed value of the resistance difference between the resistances of said second and said first elements;

means for maintaining the resistance of said first element at said desired resistance so that said resistance difference is maintained at said predetermined fixed value, the resistance of said first element varying as a function of time;

means for determining the volume mean temperature of said first element over said time period at said desired resistance of said first element, said volume mean temperature varying as a function of time;

means for determining the temperature difference between said volume mean temperature and said reference temperature over said time period, said temperature difference varying as a function of time;

means for determining the thermal conductivity of said medium over said time period in accordance with the expression:

$$k(t) = \frac{5}{\frac{\Delta T(t) R_h(t) 20\pi \bar{a}}{V_h^2(t)} - \frac{1.0}{k_b(T)}}$$

where $\Delta T(t)$ is said temperature difference, $R_h(t)$ is said resistance of said heating means at said volume mean temperature, $\bar{a}$ is the radius of a spherical heating means having a volume equivalent to the actual volume of said first element, $V_h(t)$ is the voltage at said first element when power is applied thereto, and $k_b$ is the predetermined thermal conductivity of said first element.

32. Apparatus in accordance with claim 31 wherein said data processing system includes means for determining the intrinsic thermal conductivity $k_m$ of said medium when no fluid is flowing therein;

means for determining the effective thermal conductivity $k_{eff}(t)$ of said medium when a fluid having a predetermined heat capacity is flowing therein;

means for determining the ratio of $k_{eff}(t)/k_m$ over said time period; and means for determining the rate of flow $\dot{\omega}(t)$ of said fluid in said medium in accordance with the expression:

$$\dot{\omega}(t) = \left( \frac{k_{eff}(t)}{k_m} - 1 \right)^2 \frac{k_m}{C_b \bar{a}^2}$$

where $C_b$ is said predetermined heat capacity.

* * * * *